(12) United States Patent
Brambilla et al.

(10) Patent No.: US 9,878,121 B2
(45) Date of Patent: *Jan. 30, 2018

(54) VENTILATION MASK WITH HEAT AND MOISTURE EXCHANGE DEVICE

(71) Applicant: Breathe Technologies, Inc., Irvine, CA (US)

(72) Inventors: Enrico Brambilla, Irvine, CA (US); Samir S. Ahmad, San Diego, CA (US)

(73) Assignee: BREATHE TECHNOLOGIES, INC., Irvine, CA (US)

( * ) Notice: Subject to any disclaimer, the term of this patent is extended or adjusted under 35 U.S.C. 154(b) by 559 days.

This patent is subject to a terminal disclaimer.

(21) Appl. No.: 13/800,156

(22) Filed: Mar. 13, 2013

(65) Prior Publication Data

US 2014/0276177 A1   Sep. 18, 2014

(51) Int. Cl.
| | |
|---|---|
| A61M 16/10 | (2006.01) |
| A61M 16/06 | (2006.01) |
| A61B 5/097 | (2006.01) |
| A61M 16/20 | (2006.01) |

(52) U.S. Cl.
CPC ........ *A61M 16/1045* (2013.01); *A61M 16/06* (2013.01); *A61M 16/0666* (2013.01); *A61B 5/097* (2013.01); *A61M 16/208* (2013.01)

(58) Field of Classification Search
CPC .............. A61M 16/1045; A61M 16/06; A61M 16/0666; A61M 16/208; A61B 5/097; A41D 13/00; A51F 5/08; A61F 7/00
(Continued)

(56) References Cited

U.S. PATENT DOCUMENTS

| | | |
|---|---|---|
| 53,694 A | 4/1866 | Smith |
| 53,695 A | 4/1866 | Somes |

(Continued)

FOREIGN PATENT DOCUMENTS

| | | |
|---|---|---|
| AU | 2003217098 A1 | 12/2003 |
| CA | 2193906 A1 | 6/1997 |

(Continued)

OTHER PUBLICATIONS

Exhaled Tidal Volume Overestimation in Mechanically Ventilated Patients With Large Cardiogenic Oscillation. Imanaka H, Takeuchi M, Tachibana K, Nishimura M. Crit Care Med. Jul. 2004;32(7):1546-9.

(Continued)

*Primary Examiner* — (Jackie) Tan-Uyen T Ho
*Assistant Examiner* — Margaret Luarca
(74) *Attorney, Agent, or Firm* — Stetina Brunda Garred and Brucker; Mark B. Garred

(57) ABSTRACT

In accordance with the present invention, there is provided a mask, such as a nasal pillows mask, for achieving positive pressure mechanical ventilation (inclusive of CPAP, ventilator support, critical care ventilation, emergency applications). The mask of the present invention includes a piloted exhalation valve that is used to achieve the target pressures/flows to the patient. The pilot for the valve may be pneumatic and driven from the gas supply tubing from the ventilator. The mask of the present invention further includes a heat and moisture exchange (HME) device which is directly integrated into the housing or cushion thereof (thus residing in extremely close proximity to the patient's nostrils), and is further uniquely configured to induce a flow pattern between it and the cushion which maximizes the transmission of heat and moisture to air which is inhaled by and exhaled from the patient through the mask.

16 Claims, 6 Drawing Sheets

(58) Field of Classification Search
USPC ............ 128/201.13, 201.25, 205.27, 205.29,
128/206.11, 206.12, 206.16, 206.17,
128/201.1, 200.24, 200.26, 857, 858, 863,
128/205.25, 206.21; 607/104
See application file for complete search history.

(56) References Cited

U.S. PATENT DOCUMENTS

| | | |
|---|---|---|
| 252,515 A | 1/1882 | Ebdshaw |
| 306,346 A | 10/1884 | Pabaf-Javal |
| 321,600 A | 7/1885 | Heckee |
| 430,380 A | 6/1890 | Evarts |
| 432,325 A | 7/1890 | McIntyre |
| 474,434 A | 5/1892 | Banker |
| 539,217 A | 5/1895 | Chapman |
| 546,673 A | 9/1895 | Frederick |
| 694,089 A | 2/1902 | Brewer |
| 3,326,214 A | 6/1967 | McCoy |
| 3,747,597 A | 7/1973 | Olivera |
| 3,881,482 A | 5/1975 | Lindholm et al. |
| 4,121,583 A | 10/1978 | Chen |
| 4,318,398 A | 3/1982 | Oetjen |
| 4,325,365 A | 4/1982 | Barbuto |
| 4,458,679 A | 7/1984 | Ward |
| 4,771,770 A | 9/1988 | Artemenko et al. |
| 4,787,105 A | 11/1988 | Phillips et al. |
| 4,913,140 A | 4/1990 | Orec |
| 5,062,145 A | 10/1991 | Zwaan et al. |
| 5,111,809 A | 5/1992 | Gamble et al. |
| 5,117,820 A | 6/1992 | Robitaille |
| 5,284,160 A | 2/1994 | Dryden |
| 5,367,604 A | 11/1994 | Murray |
| 5,383,447 A | 1/1995 | Lang |
| 5,433,192 A | 7/1995 | Ebeling |
| 5,435,298 A | 7/1995 | Anthony |
| 5,445,143 A | 8/1995 | Sims |
| 5,462,048 A | 10/1995 | Lambert et al. |
| 5,505,768 A | 4/1996 | Altadonna |
| 5,529,060 A | 6/1996 | Salmon et al. |
| 5,537,996 A | 7/1996 | McPhee |
| 5,537,997 A | 7/1996 | Mechlenburg et al. |
| 5,546,930 A | 8/1996 | Wikefeldt |
| 5,558,084 A | 9/1996 | Daniell et al. |
| 5,588,423 A | 12/1996 | Smith |
| 5,595,173 A | 1/1997 | Dodd |
| 5,598,837 A | 2/1997 | Sirianne et al. |
| 5,617,913 A | 4/1997 | Degregoria et al. |
| 5,640,951 A | 6/1997 | Huddart et al. |
| 5,647,344 A | 7/1997 | Turnbull |
| 5,655,522 A | 8/1997 | Mechlenburg et al. |
| 5,666,950 A | 9/1997 | Smith |
| 5,673,687 A | 10/1997 | Dobson et al. |
| 5,701,891 A | 12/1997 | Groenke |
| 5,836,303 A | 11/1998 | Hurst et al. |
| 5,848,590 A | 12/1998 | Smith |
| 5,853,884 A | 12/1998 | Nichols et al. |
| 5,964,219 A | 10/1999 | Pekka |
| 6,014,890 A | 1/2000 | Breen |
| 6,017,374 A | 1/2000 | Huxham |
| 6,050,260 A | 4/2000 | Daniell et al. |
| 6,078,730 A | 6/2000 | Huddart et al. |
| 6,095,135 A | 8/2000 | Clawson et al. |
| 6,116,235 A | 9/2000 | Walters et al. |
| 6,135,432 A | 10/2000 | Hebblewhite et al. |
| 6,201,223 B1 | 3/2001 | Nitta |
| 6,272,933 B1 | 8/2001 | Gradon et al. |
| 6,308,706 B1 | 10/2001 | Lammers et al. |
| 6,338,473 B1 | 1/2002 | Hebblewhite et al. |
| 6,349,722 B1 | 2/2002 | Gradon et al. |
| 6,363,930 B1 | 4/2002 | Clawson et al. |
| 6,394,084 B1 | 5/2002 | Nitta |
| 6,397,841 B1 | 6/2002 | Kenyon |
| 6,398,197 B1 | 6/2002 | Dickinson |
| 6,478,026 B1 | 11/2002 | Wood |
| 6,516,798 B1 | 2/2003 | Davies |
| 6,523,538 B1 | 2/2003 | Wikefeldt |
| 6,550,476 B1 | 4/2003 | Ryder |
| 6,554,260 B1 | 4/2003 | Lipscombe et al. |
| 6,557,551 B2 | 5/2003 | Nitta |
| 6,584,972 B2 | 7/2003 | McPhee |
| 6,595,215 B2 | 7/2003 | Wood |
| 6,598,604 B1 | 7/2003 | Seakins |
| 6,662,802 B2 | 12/2003 | Smith |
| 6,694,974 B1 | 2/2004 | George-Gradon et al. |
| 6,733,556 B1 | 5/2004 | Luigi |
| 6,772,758 B2 | 8/2004 | Lambert |
| 6,772,999 B2 | 8/2004 | Lipscombe et al. |
| 6,802,314 B2 | 10/2004 | McPhee |
| 6,805,120 B1 | 10/2004 | Jeffrey et al. |
| 6,863,069 B2 | 3/2005 | Wood |
| 6,918,389 B2 | 7/2005 | Seakins et al. |
| 6,921,417 B2 | 7/2005 | Persson et al. |
| 6,935,337 B2 | 8/2005 | Virr et al. |
| 6,953,354 B2 | 10/2005 | Edirisuriya |
| 6,976,488 B2 | 12/2005 | Halperin |
| 6,990,977 B1 | 1/2006 | Calluaud |
| 6,994,089 B2 | 2/2006 | Wood |
| 7,032,592 B2 | 4/2006 | Castor |
| 7,043,979 B2 | 5/2006 | Smith |
| 7,051,733 B2 | 5/2006 | Gradon et al. |
| 7,069,928 B1 | 7/2006 | Waldo, Jr. |
| 7,086,399 B2 | 8/2006 | Makinson et al. |
| 7,106,955 B2 | 9/2006 | Thudor et al. |
| 7,111,624 B2 | 9/2006 | Thudor et al. |
| 7,120,354 B2 | 10/2006 | Mackie et al. |
| 7,137,388 B2 | 11/2006 | Virr et al. |
| 7,140,367 B2 | 11/2006 | White |
| 7,146,979 B2 | 12/2006 | Seakins et al. |
| 7,192,550 B2 | 3/2007 | Berger et al. |
| RE39,724 E | 7/2007 | Gradon et al. |
| 7,237,770 B2 | 7/2007 | Lipscombe et al. |
| 7,263,994 B2 | 9/2007 | Gradon et al. |
| 7,306,205 B2 | 12/2007 | Huddart et al. |
| 7,396,995 B2 | 7/2008 | Laurent et al. |
| 7,428,902 B2 | 9/2008 | Du et al. |
| 7,481,222 B2 | 1/2009 | Reissmann |
| 7,493,902 B2 | 2/2009 | White et al. |
| 7,506,647 B2 | 3/2009 | Worthington |
| 7,525,663 B2 | 4/2009 | Kwok et al. |
| RE40,806 E | 6/2009 | Gradon et al. |
| 7,549,419 B2 | 6/2009 | Carlsen et al. |
| 7,588,029 B2 | 9/2009 | Smith et al. |
| 7,594,509 B2 | 9/2009 | Burk |
| 7,614,398 B2 | 11/2009 | Virr et al. |
| 7,616,871 B2 | 11/2009 | Kramer |
| 7,624,731 B2 | 12/2009 | Walstrom |
| 7,634,998 B1 | 12/2009 | Fenley |
| 7,849,852 B2 | 12/2010 | Bremner et al. |
| 7,870,857 B2 | 1/2011 | Dhuper et al. |
| 7,913,497 B2 | 3/2011 | Dickerson |
| 7,913,640 B2 | 3/2011 | MacDonald et al. |
| 7,926,485 B2 | 4/2011 | Nguyen et al. |
| 7,958,891 B2 | 6/2011 | Smith et al. |
| 7,962,018 B2 | 6/2011 | Hunt et al. |
| 7,997,270 B2 | 8/2011 | Meier et al. |
| 8,006,691 B2 | 8/2011 | Kenyon et al. |
| 8,015,971 B2 | 9/2011 | Kwok |
| 8,020,551 B2 | 9/2011 | Virr et al. |
| 8,028,693 B2 | 10/2011 | Trevor-Wilson et al. |
| 8,037,882 B2 | 10/2011 | Smith et al. |
| 8,042,535 B2 | 10/2011 | Kenyon et al. |
| 8,052,127 B2 | 11/2011 | Nichols et al. |
| 8,469,031 B2 * | 6/2013 | Winter et al. ............ 128/205.24 |
| 2002/0083947 A1 | 7/2002 | Seakins |
| 2003/0079748 A1 | 5/2003 | Seakins |
| 2003/0116163 A1 | 6/2003 | Wood |
| 2004/0211421 A1 | 10/2004 | Blansfield |
| 2007/0062534 A1 | 3/2007 | Fisher et al. |
| 2007/0079826 A1 | 4/2007 | Kramer et al. |
| 2007/0277825 A1 | 12/2007 | Bordewick et al. |
| 2008/0099013 A1 | 5/2008 | Graham |
| 2008/0105257 A1 | 5/2008 | Klasek et al. |
| 2008/0190436 A1 | 8/2008 | Jaffe et al. |
| 2008/0223367 A1 | 9/2008 | Cox et al. |

(56) References Cited

U.S. PATENT DOCUMENTS

| | | |
|---|---|---|
| 2008/0302361 A1 | 12/2008 | Snow et al. |
| 2009/0000620 A1 | 1/2009 | Virr |
| 2009/0095295 A1 | 4/2009 | Wruck et al. |
| 2009/0114221 A1 | 5/2009 | Nagorny |
| 2009/0151728 A1 | 6/2009 | McConnell et al. |
| 2009/0174092 A1 | 7/2009 | Kwok |
| 2009/0194106 A1 | 8/2009 | Smith et al. |
| 2009/0217929 A1 | 9/2009 | Kwok et al. |
| 2009/0223514 A1 | 9/2009 | Smith et al. |
| 2009/0229606 A1 | 9/2009 | Tang et al. |
| 2009/0241948 A1 | 10/2009 | Clancy et al. |
| 2009/0301478 A1 | 12/2009 | Ohmura et al. |
| 2009/0320840 A1 | 12/2009 | Klasek et al. |
| 2009/0320851 A1 | 12/2009 | Selvarajan et al. |
| 2010/0018534 A1 | 1/2010 | Veliss et al. |
| 2010/0071693 A1 | 3/2010 | Allum et al. |
| 2010/0083965 A1 | 4/2010 | Virr et al. |
| 2010/0147299 A1 | 6/2010 | Row et al. |
| 2010/0154796 A1 | 6/2010 | Smith et al. |
| 2010/0206308 A1 | 8/2010 | Klasek et al. |
| 2010/0282247 A1 | 11/2010 | Kadrichu et al. |
| 2011/0017212 A1 | 1/2011 | Kenyon et al. |
| 2011/0023874 A1 | 2/2011 | Bath et al. |
| 2011/0023877 A1 | 2/2011 | Kenyon et al. |
| 2011/0120462 A1 | 5/2011 | Tatkov et al. |
| 2011/0162647 A1 | 7/2011 | Huby et al. |
| 2011/0253136 A1 | 10/2011 | Sweeney et al. |
| 2011/0283999 A2 | 11/2011 | Smith et al. |
| 2011/0297150 A1 | 12/2011 | Kwok |
| 2012/0138050 A1 | 6/2012 | Wondka et al. |
| 2012/0209096 A1 | 8/2012 | Jaffe et al. |
| 2012/0325205 A1 | 12/2012 | Allum et al. |

FOREIGN PATENT DOCUMENTS

| | | |
|---|---|---|
| CN | 1878589 A | 12/2006 |
| DE | 69211011 T2 | 12/1996 |
| DE | 69724996 T2 | 7/2004 |
| DE | 60213428 T2 | 3/2007 |
| DE | 60031249 T2 | 5/2007 |
| DE | 60215955 T2 | 6/2007 |
| DE | 60213427 T2 | 9/2007 |
| EP | 265163 A3 | 2/1989 |
| EP | 504977 A1 | 9/1992 |
| EP | 409402 B1 | 8/1993 |
| EP | 588214 B1 | 12/1998 |
| EP | 604399 B1 | 12/1998 |
| EP | 1005878 A2 | 6/2000 |
| EP | 1100591 B1 | 11/2004 |
| EP | 1629859 A1 | 3/2006 |
| EP | 1042034 B1 | 2/2008 |
| EP | 2039387 A8 | 11/2009 |
| EP | 2113275 A1 | 11/2009 |
| EP | 2229973 A3 | 11/2010 |
| EP | 2269681 A2 | 1/2011 |
| EP | 2272557 A2 | 1/2011 |
| EP | 2296740 A1 | 3/2011 |
| EP | 2301615 A1 | 3/2011 |
| WO | 2008113424 A1 | 9/2008 |
| WO | 2009118718 A1 | 10/2009 |
| WO | WO2009125539 | 10/2009 |
| WO | 2009149284 A1 | 12/2009 |
| WO | 2009149289 A1 | 12/2009 |
| WO | 2009149290 A1 | 12/2009 |
| WO | 2010096467 A1 | 8/2010 |
| WO | WO2015013761 | 2/2015 |

OTHER PUBLICATIONS

[Phoning Study About Postoperative Practice and Application of Non-Invasive Ventilation]. Chanques G, Jaber S, Delay JM, Perrigault PF, Lefrant JY, Eledjam JJ. Ann Fr Anesth Reanim. Dec. 2003;22(10):879-85.

Sudden Complete Obstruction of Breathing Circuit During Postural Change Upon Completion of Thoracic Spinal Surgery in a Pediatric Patient. Wang YM, Chen CS, Chung NC, Ye XD, Liu K. Acta Anaesthesiol Sin. Sep. 2003;41(3):145-8.

Influence of the Humidification Device During Acute Respiratory Distress Syndrome. Prat G, Renault A, Tonnelier JM, Goetghebeur D, Oger E, Boles JM, L'Her E. Intensive Care Med. Dec. 2003;29(12):2211-5. Epub Aug. 6, 2003.

Mechanical Effects of Airway Humidification Devices in Difficult to Wean Patients. Girault C, Breton L, Richard JC, Tamion F, Vandelet P, Aboab J, Leroy J, Bonmarchand G. Crit Care Med. May 2003;31(5):1306-11.

A New Heat and Moisture Exchanger, Trach-Vent Plus, for Patients With Spontaneous Respiration]. Nishiyama T, Hanaoka K. Masui. Apr. 2003;52(4):417-9.

The Effect of Heat and Moisture Exchanger on Humidity and Body Temperature in a Low-Flow Anaesthesia System. Johansson A, Lundberg D, Luttropp HH. Acta Anaesthesiol Scand. May 2003;47(5):564-8.

The Effect of Heat and Moisture Exchanger and Gas Flow on Humidity and Temperature in a Circle Anaesthetic System. Poopalalingam R, Goh MH, Chan YW. Singapore Med J. Nov. 2002;43(11):563-5.

Ability and Safety of a Heated Humidifier to Control Hypercapnic Acidosis in Severe Ards. Prin S, Chergui K, Augarde R, Page B, Jardin F, Vieillard-Baron A. Intensive Care Med. Dec. 2002;28(12):1756-60. Epub Oct. 8, 2002.

The Combination of a Heat and Moisture Exchanger and a Booster: A Clinical and Bacteriological Evaluation Over 96 H. Thomachot L, Viviand X, Boyadjiev I, Vialet R, Martin C. Intensive Care Med. Feb. 2002;28(2):147-53. Epub Jan. 12, 2002.

Efficiency and Safety of Mechanical Ventilation With a Heat and Moisture Exchanger Changed Once a Week. Paluch B. Am J Respir Crit Care Med. Nov. 15, 2001;164(10 Pt 1):1999-2000. 66 a Breathing Circuit Disconnection Detected by Anesthetic Agent Monitoring. Kennedy RR, French RA Can J Anaesth. Oct. 2001;48(9):847-9.

A Randomized Clinical Trial to Compare the Effects of a Heat and Moisture Exchanger With a Heated Humidifying System on the Occurrence Rate of Ventilator-Associated Pneumonia Memish ZA, Oni GA, Djazmati W, Cunningham G, Mah MW. Am J Infect Control. Oct. 2001;29(5):301-5.

[Measurement of Water Vapour Pressure in the Airways of Mechanically Ventilated Patient Using Different Types of Humidifiers]. Rathgeber J, Betker T, Züchner K. Anasthesiol Intensivmed Notfallmed Schmerzther. Sep. 2001;36(9):560-5.

[Experience With the Hme-Provox Stomafilter in Laryngectomized Patients]. Herranz González-Botas J, Suárez T, Garcia Carreira B, Martínez Morán A. Acta Otorrinolaringol Esp. Apr. 2001;52(3):221-5.

Air Flow Resistance of Three Heat and Moisture Exchanging Filter Designs Under Wet Conditions: Implications for Patient Safety. Morgan-Hughes NJ, Mills GH, Northwood D. Br J Anaesth. Aug. 2001;87(2):289-91.

A New Device to Reduce the Consumption of a Halogenated Anaesthetic Agent. Enlund M, Wiklund L, Lambert H. Anaesthesia. May 2001;56(5):429-32. Intensive Care Med. Jan. 2001;27(1):296-300.

Changing Patterns of Airway Accidents in Intubated Icu Patients. Kapadia FN, Bajan KB, Singh S, Mathew B, Nath A, Wadkar S. Intensive Care Med. Jan. 2001;27(1):296-300.

Retention of Airborne Latex Particles by a Bacterial and Viral Filter Used in Anaesthesia Apparatus. Barbara J, Chabane MH, Leynadier F, Girard F. Anaesthesia. Mar. 2001;56(3):231-4.

Measurement of Tracheal Temperature Is Not a Reliable Index of Total Respiratory Heat Loss in Mechanically Ventilated Patients. Thomachot L, Viviand X, Lagier P, Dejode JM, Albanèse J, Martin C. Crit Care. 2001;5(1):24-30. Epub Dec. 8, 2000.

A Randomized, Controlled, Clinical Trial of a Chemically-Reactive Heated Humidifier. Broach SD, Durbin CG Jr. Respir Care. Jan. 2001;46(1):37-42.

(56) References Cited

OTHER PUBLICATIONS

Mechanical Effects of Heat-Moisture Exchangers in Ventilated Patients. Iotti GA, Olivei MC, Braschi A. Crit Care. 1999;3(5):R77-82. Epub Sep. 23, 1999.
A New Device for 100 Per Cent Humidification of Inspired Air. Larsson A, Gustafsson A, Svanborg L. Crit Care. 2000;4(1):54-60. Epub Jan. 24, 2000.
Technical Requirements for Buying a Heat and Humidity Exchanger for Ventilation During Anesthesia. French Society of Anesthesia and Intensive Care Najjar J, Loctin H, Goullet D. Ann Fr Anesth Reanim. Aug. 2000;19(7):556-60.
The Effect of a Heat and Moisture Exchanger on Gas Flow in a Mapleson F Breathing System During Inhalational Induction. Da Fonseca JM, Wheeler DW, Pook JA. Anaesthesia. Jun. 2000;55(6):571-3.
The Effects of Passive Humidifier Dead Space on Respiratory Variables in Paralyzed and Spontaneously Breathing Patients. Campbell RS, Davis K Jr, Johannigman JA, Branson RD. Respir Care. Mar. 2000;45(3):306-12.
Hypercapnia Due to a Heat and Moisture Exchanger. Briassoulis G, Paraschou D, Hatzis T. Intensive Care Med. Jan. 2000;26(1):147.
Changing a Hydrophobic Heat and Moisture Exchanger After 48 Hours Rather Than 24 Hours: A Clinical and Microbiological Evaluation. Boisson C, Viviand X, Arnaud S, Thomachot L, Miliani Y, Martin C. Intensive Care Med. Nov. 1999;25(11):1237-43.
Humidification Method That Decreases Condensate Contamination in Ventilator Tubing. Austan F, Suzukawa M. Heart Lung. Jan.-Feb. 2000;29(1):56-9.
Supplementary Oxygen and the Laryngeal Mask Airway—Evaluation of a Heat-And-Moisture Exchanger. Orme RM, Williams M. Anaesth Intensive Care. Oct. 1999;27(5):509-11.
Changing Heat and Moisture Exchangers Every 48 Hours Does Not Increase the Incidence of Nosocomial Pneumonia Daumal F, Colpart E, Manoury B, Mariani M, Daumal M. Infect Control Hosp Epidemiol. May 1999;20(5):347-9.
Critical Incident Involving a Heat and Moisture Exchanger With Attached Flexible Connector. Mansor M, Chan L. Anaesth Intensive Care. Feb. 1999;27(1):114-5.
[Prevention of Contamination With a Heat-And-Moisture-Exchanger (Hme) and Bacterial Filter During Clinical Anesthesia]. Shibata M, Asano M. Masui. Dec. 1998;47(12):1464-70.
The Influence of Stoma Occlusion on Aspects of Tracheoesophageal Voice. van As CJ, Hilgers FJ, Koopmansvan Beinum FJ, Ackerstaff AH. Acta Otolaryngol. Sep. 1998;118(5):732-8.
Preservation of Humidity and Heat of Respiratory Gases in Spontaneously Breathing, Tracheostomized Patients. Thomachot L, Viviand X, Arnaud S, Vialet R, Albanese J, Martin C. Acta Anaesthesiol Scand. Aug. 1998;42(7):841-4.
Humidification Practices in the Adult Intensive Care Unit, Prince of Wales Hospital. Lawrence JC. Respir Care Clin N Am. Jun. 1998;4(2):301-4.
Charcoal As an Airway Isoflurane Reflection Filter. Dahm SL, Steptoe P, Luttropp HH, Reinstrup P. Eur J Anaesthesiol. Mar. 1998;15(2):230-3.
Efficacy of Heat and Moisture Exchangers After Changing Every 48 Hours Rather Than 24 Hours. Thomachot L, Vialet R, Viguier JM, Sidier B, Roulier P, Martin C. Crit Care Med. Mar. 1998;26(3):477-81.
Inhalation Rewarming From Hypothermia: An Evaluation in −20 Degrees C Simulated Field Conditions. Mekjavi_ IB, Eiken O. Aviat Space Environ Med. May 1995;66(5):424-9.
Mechanical Ventilation With Heated Humidifiers or Heat and Moisture Exchangers: Effects on Patient Colonization and Incidence of Nosocomial Pneumonia. Dreyfuss D, Djedaïni K, Gros I, Mier L, Le Bourdellés G, Cohen Y, Estagnasié P, Coste F, Boussougant.
Use of a Heat and Moisture Exchanger During Long-Term Mechanical Ventilation. Sottiaux T. Chest. Sep. 1992;102(3):979-80.

[Are Humidity Filters Necessary in the Inspired Air in the Breathing Circuit? A New In Vivo Method of Measuring Humidity in the Air Breathed] Kohler P, Rimek A, Albrecht M, Frankenberger H, Merlins W, van Ackern K.
Do Heated Humidifiers and Heat and Moisture Exchangers Prevent Temperature Drop During Lower Abdominal Surgery? Goldberg ME, Epstein R, Rosenblum F, Larijani GE, Marr A, Lessin J, Torjman M, Seltzer J.
The Influence of a Heat and Moisture Exchanger (Hme) on the Respiratory Symptoms After Total Laryngectomy. Hilgers FJ, Aaronson NK, Ackerstaff AH, Schouwenburg PF, van Zandwikj N.
The Use of an Artificial Nose (Hme: Heat-Moisture Exchanger) in Controlled Ventilation]. Sottiaux T. Rev Med Liege. Apr. 1991;46(4):204-12.
[Physical and Psychosocial Sequelae of Total Larynx Extirpation and the Use of a Heat and Moisture Exchanger]. Ackerstaff AH, Hilgers FJ, Aaronson NK, Schouwenburg PF, van Zandwijk N.
[Experimental Evaluation of a Prototype of Absolute Antibacterial Filter As a Moisture and Heat Exchanger]. Elena A, Solca M, Croci M, Noto A. Minerva Anestesiol. Oct. 1990;56(10):1253-4.
[Anesthetic Management of a Patient With Sjögren'S Syndrome and Pulmonary Fibrosis]. Takahashi S, Ogasawara H, Tsubo T, Ishihara H, Matsuki A. Masui. Oct. 1990;39(10):1393-6.
Heat and Moisture Exchangers and the Body Temperature: A Peroperative Study. Eckerbom B, Lindholm CE. Acta Anaesthesiol Scand. Oct. 1990;34(7):538-42.
Maintenance of Body Temperature in Elderly Patients Who Have Joint Replacement Surgery. A Comparison Between the Heat and Moisture Exchanger and Heated Humidifier Yam PC, Carli F. Anaesthesia. Jul. 1990;45(7):563-5.
Complications Related to the Use of a Heat and Moisture Exchanger. Prasad KK, Chen L. Anesthesiology. May 1990;72(5):958.
153 Passive Warming of Airway Gases (Artificial Nose) Improves Accuracy of Esophageal Temperature Monitoring. Siegel MN, Gravenstein N. J Clin Monit. Apr. 1990;6(2):89-92.
Heat and Moisture Exchangers and Vaporizing Humidifiers in the Intensive Care Unit. Martin C, Perrin G, Gevaudan MJ, Saux P, Gouin F. Chest. Jan. 1990;97(1):144-9.
Bacterial Contamination and Frequency of Changing Ventilator Circuitry. Cadwallader HL, Bradley CR, Ayliffe GA J Hosp Infect. Jan. 1990;15(1):65-72.
Passive or Active Inspired Gas Humidification Increases Thermal Steady-State Temperatures in Anesthetized Infants. Bissonnette B, Sessler DI. Anesth Analg. Dec. 1989;69(6):783-7.
A Dangerous Defect in a Heat and Moisture Exchanger. Prados W. Anesthesiology. Nov. 1989;71(5):804.
Tracheal Tube Biofilm As a Source of Bacterial Colonization of the Lung. Inglis TJ, Millar MR, Jones JG, Robinson DA. J Clin Microbiol. Sep. 1989;27(9):2014-8.
Passive and Active Inspired Gas Humidification in Infants and Children. Bissonnette B, Sessler DI, LaFlamme P Anesthesiology. Sep. 1989;71(3):350-4.
Failure of a Heat and Moisture Exchanger As a Cause of Disconnection During Anaesthesia. Bengtsson M, Johnson A. Acta Anaesthesiol Scand. Aug. 1989;33(6):522-3.
Intraoperative Temperature Monitoring Sites in Infants and Children and the Effect of Inspired Gas Warming on Esophageal Temperature Bissonnette B, Sessler DI, LaFlamme P. Anesth Analg. Aug. 1989;69(2):192-6.
Physiological Effects of a Mouth-Borne Heat Exchanger During Heavy Exercise in a Cold Environment. Eiken O, Kaiser P, Holmér I, Baer R. Ergonomics. Jun. 1989;32(6):645-53.
Study of Humidification Potential of a Heat and Moisture Exchanger in Tracheotomized Dogs. Myer CM 3rd, McDonald JS, Hubbell RN, Stith J. Ann Otol Rhinol Laryngol. May-Jun. 1988;97(3 Pt 1):322-5.
Endotracheal Tube Occlusion Associated With the Use of Heat and Moisture Exchangers in the Intensive Care Unit. Cohen IL, Weinberg PF, Fein IA, Rowinski GS. Crit Care Med. Mar. 1988;16(3):277-9.

(56) References Cited

OTHER PUBLICATIONS

The Heat and Moisture Exchanger Does Not Preserve Body Temperature or Reduce Recovery Time in Outpatients Undergoing Surgery and Anesthesia. Goldberg ME, Jan R, Gregg CE, Berko R, Marr AT, Larijani GE. Anesthesiology. Jan. 1988;68(1):122-3.
Effectiveness of a Heat and Moisture Exchanger in Preventing Hyperpnoea Induced Bronchoconstriction in Subjects With Asthma. Gravelyn TR, Capper M, Eschenbacher WL. Thorax. Nov. 1987;42(11):877-80.
An Evaluation of Six Disposable Heat and Moisture Exchangers. Turtle MJ, Ilsley AH, Rutten AJ, Runciman WB. Anaesth Intensive Care. Aug. 1987;15(3):317-22.
Contamination Control in Long-Term Ventilation. A Clinical Study Using a Heat- and Moisture-Exchanging Filter. Gallagher J, Strangeways JE, Allt- Graham J. Anaesthesia. May 1987;42(5):476-81.
Effects of a Heat and Moisture Exchanger on Carbon Dioxide Equilibrium During Mechanical Ventilation With the Bain Circuit. Romano E, Gullo A, Vacri A, Bonifacio R, Caristi D. Eur J Anaesthesiol. May 1987;4(3):183-6.
The Heat and Moisture Exchanger in Post-Tracheotomy Care. Myer CM 3rd. Otolaryngol Head Neck Surg. Feb. 1987;96(2):209-10.
Moistening of Inspired Air During Respirator Treatment. Comparison Between the Water-Bath Evaporator and Hygroscopic Moisture Heat Exchanger]. Kirkegaard L, Andersen BN, Jensen S. Ugeskr Laeger. Jan. 12, 1987;149(3):152-5.
Portable Lung Ventilators: The Potential Risk From Bacterial Colonisation. Shelly MP, Park GR, Warren RE, Whetstone RJ. Intensive Care Med. 1986;12(4):328-31.
Long-Term Compliance of Laryngectomized Patients With a Specialized Pulmonary Rehabilitation Device: Provox Stornafilter. Ackerstaff AH, Hilgers FJ, Balm AJ, Tan IB. Laryngoscope. Feb. 1998;108(2):257-60.
Clinical Utility of Hygroscopic Heat and Moisture Exchangers in Intensive Care Patients. Boots RJ, Howe S, George N, Harris FM, Faoagali J. Crit Care Med. Oct. 1997;25(10):1707-12.
Correlation Between Simple Clinical Parameters and the In Vitro Humidification Characteristics of Filter Heat and Moisture Exchangers. Groupe De Travail Sur Les Respirateurs. Beydon L, Tong D, Jackson N, Dreyfuss D. Chest. Sep. 1997;112(3):739-44.
Unfavorable Mechanical Effects of Heat and Moisture Exchangers in Ventilated Patients. Iotti GA, Olivei MC, Palo A, Galbusera C, Veronesi R, Comelli A, Brunner JX, Braschi A. Intensive Care Med. Apr. 1997;23(4):399-405.
Acute Intraoperative Endotracheal Tube Obstruction Associated With a Heat and Moisture Exchanger in an Infant. Casta A, Houck CS. Anesth Analg. Apr. 1997;84(4):939-40.
Safety of Combined Heat and Moisture Exchanger Filters in Long-Term Mechanical Ventilation. Hurni JM, Feihl F, Lazor R, Leuenberger P, Perret C. Chest. Mar. 1997;111(3):686-91.
Patient Ventilator Interfaces: Practical Aspects in the Chronic Situation. Clini E. Monaldi Arch Chest Dis. Feb. 1997;52(1):76-9.
The Effect of a Heat and Moisture Exchanger on Humidity in a Low-Flow Anaesthesia System. Henriksson BA, Sundling J, Hellman. Anaesthesia. Feb. 1997;52(2):144-9 108 [Artificial Humidification of Inspired Gas—Status of Knowledge and Technique]. Henze D, Menzel M, Radke J. Anaesthesiol Reanim. 1997;22(6):153-8. 109 The Benefit of Using a Heat and Moisture Exchanger During Short Operations in Young Children. Monrigal JP, Granry JC. Paediatr Anaesth. 1997;7(4):295-300.
Remarks on the Work of J. Rathgeber Et Al. Respiratory Gas Acclimatization With an Efficient Hme (Heat and Moisture Exchanger)—An Effective and Cost Saving Alternative to Active Humidifying of the Ventilated Patient. Anaesthesist (1996) 45: 518-525 Thäle H, Hares W. Anaesthesist. Dec. 1996;45(12):1270-2.
The Effect of Convection Warming During Abdominal Surgery on the Early Postoperative Heat Balance]. Kaudasch G, Schempp P, Skierski P, Turner E. Anaesthesist. Nov. 1996;45(11):1075-81.

A New Heat and Moisture Exchanger With Speech Valve (Provox Stomafilter). Hilgers FJ, Ackerstaff AH, Balm AJ, Gregor RT. Clin Otolaryngol Allied Sci. Oct. 1996;21(5):414-8.
[the Effect of a Heat and Moisture Exchanger (Hme) on Bronchial Mucus Transport in a Closed Inhalation Anesthesia System]. Konrad F, Mezödy M, Goertz A, Marx T, Georgieff M. Anaesthesist. Sep. 1996;45(9):802-6.
Failure of Ventilation in an Infant Due to Increased Resistance of a Disposable Heat and Moisture Exchanger. Barnes SD, Normoyle DA. Anesth Analg. Jul. 1996;83(1):193.
[Air Conditioning With a High-Performance Hme (Heat and Moisture Exchanger)—An Effective and Economical Alternative to Active Humidifiers in Ventilated Patients. A Prospective and Randomized Clinical Study]. Rathgeber J, Henze D, Züchner K. Anaesthesist. Jun. 1996;45(6):518-25.
Monitoring Body-Core Temperature From the Trachea: Comparison Between Pulmonary Artery, Tympanic, Esophageal, and Rectal Temperatures. Hayes JK, Collette DJ, Peters JL, Smith KW. J Clin Monit. May 1996;12(3):261-9.
Control of Body Temperature During Abdominal Aortic Surgery. Gregorini P, Cangini D. Acta Anaesthesiol Scand. Feb. 1996;40(2):187-90.
[Microbiological Studies of a Nasal Positive Pressure Respirator With and Without a Humidifier System]. Hetzel J, Herb S, Hetzel M, Rusteberg T, Kleiser G, Weber J, Kochs M, Hombach V. Wien Med Wochenschr. 1996;146(13-14):354-6.
Shivering and Rewarming After Cardiac Surgery: Comparison of Ventilator Circuits With Humidifier and Heated Wires to Heat and Moisture Exchangers. McEvoy MT, Carey TJ. Am J Crit Care. Jul. 1995;4(4):293-9.
A Hazardous Modification of a Heat and Moisture Exchanger. Ferguson AJ, Orr DA. Anaesthesia. May 1995;50(5):479.
Inhalation Rewarming From Hypothermia: An Evaluation in −20 Degrees C Simulated Field Conditions. Mekjavi_IB, Eiken O. Aviat Space Environ Med. May 1995;66(5):424-9.
Preservation of Humidity and Heat of Respiratory Gases in Patients With a Minute Ventilation Greater Than 10 L/Min. Martin C, Papazian L, Perrin G, Saux P, Gouin F. Crit Care Med. Nov. 1994;22(11):1871-6.
Bair Hugger Forced-Air Warming Maintains Normothermia More Effectively Than Thermo-Lite Insulation. Borms SF, Engelen SL, Himpe DG, Suy MR, Theunissen WJ. J Clin Anesth. Jul.-Aug. 1994;6(4):303-7.
Improvements in Respiratory and Psychosocial Functioning Following Total Laryngectomy by the Use of a Heat and Moisture Exchanger Ackerstaff AH, Hilgers FJ, Aaronson NK, Balm AJ, van Zandwijk N. Ann Otol Rhinol Laryngol. Nov. 1993;102(11):878-83.
Oesophageal Thermal Tube for Intraoperative Hypothermia in Liver Transplantation. Steib A, Beller JP, von Bandel M, Beck F, Chabrol JL, Otteni JC. Acta Anaesthesiol Scand. Feb. 1993;37(2):199-202.
Performance of a Hydrophobic Heat and Moisture Exchanger At Different Ambient Temperatures. Croci M, Elena A, Solca M. Intensive Care Med. 1993;19(6):351-2.
An Active Heat and Moisture Exchanger. Kapadia F, Shelly MP, Anthony JM, Park GR. Br J Anaesth. Dec. 1992;69(6):640-2.
Effects of Surgical Site and Inspired Gas Warming Devices on Body Temperature During Lower Abdominal and Thoracic Surgery. Harioka T, Sone T, Nomura K, Kakuyama M. J Anesth. Oct. 1992;6(4):467-73.
Heat and Moisture Exchangers With Bacterial Filters: A Laboratory Evaluation. Mebius C. Acta Anaesthesiol Scand. Aug. 1992;36(6):572-6.
[Is the Lithium Chloride-Coated Heat and Moisture Exchanger a Danger for Patients?]. Rathgeber J, Zielmann S, Kietzmann D, Züchner K, Warnecke G. Anaesthesist. Apr. 1992;41(4):204-7.
Disablement of a Ventilator Disconnect Alarm by a Heat and Moisture Exchanger. Milligan KA. Anaesthesia. Mar. 1992;47(3):279.
Comparison of Hydrophobic Heat and Moisture Exchangers With Heated Humidifier During Prolonged Mechanical Ventilation. Roustan JP, Kienlen J, Aubas P, Aubas S, du Cailar J. Intensive Care Med. 1992;18(2):97-100.

(56) References Cited

OTHER PUBLICATIONS

Effect of a Passive Heat and Moisture Exchanger on Esophageal Temperature in Tumor-Bearing Dogs During Whole-Body Hyperthermia Meyer RE, Page RL, Thrall DE. Am J Vet Res. Oct. 1991;52(10):1688-91.
Heat and Moisture Exchanger Vs Heated Humidifier During Long-Term Mechanical Ventilation. A Prospective Randomized Study. Misset B, Escudier B, Rivara D, Leclercq B, Nitenberg G. Chest. Jul. 1991;100(1):160-3.
[Treatment of Primary and Secondary Therapy Failure in Patients With Sleep Apnea Treated With Nasal Cpap]. Becker H, Fett I, Nees E, Peter JH, von Wichert P. Pneumologie. May 1991;45 Suppl 1:301-5.
Mucociliary Transport With and Without the Use of a Heat and Moisture Exchanger. An Animal Study. The importance to mucociliary transport (MCT) and the condition of the mucus of using a heat and Acta Anaesthesiol Scand. May 1991;35(4):297-301.
[the Use of an Artificial Nose (Hme: Heat-Moisture Exchanger) in Controlled Ventilation]. Sottiaux T. Rev Med Liege. Apr. 1991;46(4):204-12.
Assessment of a Hygroscopic Heat and Moisture Exchanger for Paediatric Use. Wilkinson KA, Cranston A, Hatch DJ, Fletcher ME. Assessment of a hygroscopic heat and moisture exch . . . [Anaesthesia. 1991]—PubMed result.
[Changes in Ventilation During Use of Heat and Humidity Exchangers]. Croci M, Corrado F, Sibilla E, Tiby A, Vercesi G, Proietti D, Vannucci A. Minerva Anestesiol. Jan.-Feb. 1991;57(1-2):13-6.
Heated Humidification in Major Abdominal Surgery. Linko K, Honkavaara P, Nieminen MT. Eur J Anaesthesiol. Sep. 1984;1(3):285-91.
The Pall Ultipor Breathing Circuit Filter—An Efficient Heat and Moisture Exchanger. Chalon J, Markham JP, Ali MM, Ramanathan S, Turndorf H Anesth Analg. Jun. 1984;63(6):566-70.
The Hygroscopic Condenser Humidifier. A New Device for General Use in Anaesthesia and Intensive Care. Gedeon A, Mebius C. Anaesthesia. Nov.-Dec. 1979;34(10):1043-7.
The Foam Nose—A New Disposable Heat and Moisture Exchanger. A Comparison With Other Similar Devices. Revenäs B, Lindholm CE. Acta Anaesthesiol Scand. Feb. 1979;23(1):34-9.
A Disposable Condenser Humidifier for Use During Anaesthesia. Steward DJ. Can Anaesth Soc J. Mar. 1976;23(2):191-5.
Effects of Dry Air and Subsequent Humidification on Tracheal Mucous Velocity in Dogs. Hirsch JA, Tokayer JL, Robinson MJ, Sackner MA. J Appl Physiol. Aug. 1975;39(2):242-6.
A Reappraisal of the Multiple Gauze Heat and Moisture Exchanger. Shanks CA, Sara CA. Anaesth Intensive Care. Aug. 1973;1(5):428-32.
The Resistance to Airflow Caused by Heat and Moisture Exchanger and by Artificial Airways. Heinonen J, Poppius H. Ann Chir Gynaecol Fenn. 1969;58(1):32-5.
Heat and Moisture Exchanger As a Potential Cause of Undue Resistance to Breathing. Heinonen J, Ertama P, Poppius H. Ann Chir Gynaecol Fenn. 1969;58(2):176-9.
A Heat-And-Moisture Exchanger for Posttracheotomy Care. An Experimental Study. Toremalm NG. Acta Otolaryngol. Nov.-Dec. 1960;52:461-72.
Ecogeographic Variation in Human Nasal Passages. YokleY TR. Am J Phys Anthropol. Jan. 2009;138(1):11-22.
Performance of Breathing Filters Under Wet Conditions: A Laboratory Evaluation. Turnbull D, Fisher PC, Mills GH, Morgan-Hughes NJ. Br J Anaesth. May 2005;94(5):675-82. Epub Feb. 25, 2005.
Comparison of the Effects of Heat and Moisture Exchangers and Heated Humidifiers on Ventilation and Gas Exchange During Weaning Trials From Mechanical Ventilation Le Bourdellès G, Mier L, Fiquet B, Djedaïni K, Saumon G, Coste F, Dreyfuss D.
Heat and Moisture Exchangers. Structure and Function. Wilkes AR. Respir Care Clin N Am. Jun. 1998;4(2):261-79.

[Effect of a Heat and Humidity Exchanger (Humid-Vent-Mini) on the Carbon Dioxide Washout Effect of a Neonatal Ventilation Model]. Nikischin W. Monatsschr Kinderheilkd. Sep. 1990;138(9):593-5.
[Humidification of the Respiratory Tract in Anesthesia]. d'Athis F, de la Coussaye JE. Ann Fr Anesth Reanim. 1988;7(5):393-400.
Effect of Heat and Moisture Exchanger (Hme) Positioning on Inspiratory Gas Humidification Daisuke Inui , Jun Oto and Masaji Nishimura BMC Pulmonary Medicine 2006, 6:19.
Total Laryngectomee Rehabilitation and Hmes na http://www.webwhispers.org/library/HMEHeatMoistureExchange.asp.
Equipment Review: Mechanical Effects of Heat-Moisture Exchangers in Ventilated Patients Giorgio A lotti,1 Maddalena C Olivei,2 and Antonio Braschi Crit Care. 1999; 3(5): R77-R82.
Heat Moisture Exchanger NA http://www.nextag.com/heat-moisture-exchanger/products-html.
Heat and Moisture Exchangers (Hme) NA http://www.gehealthcare.com/euen/anesthesia/products/airway-managementaccesories-supplies/heat-moisture-exchangers/index.html.
Heat and Moisture Exchange Devices: Are They Doing What They Are Supposed to Do? Harry J. M. Lemmens, MD PhD and John G. Brock-Utne, MD PhD http://www.anesthesia-analgesia.org/content/98/2/382.full.
Heat Moisture Exchanger (HME)—Adult NA http://www.gvs.it/flex/cm/pages/ServeBLOB.php/L/UK/IDPagina/211.
Kimberly-Clark Ballard Heat and Moisture Exchangers and Filters NA http://vap.kchealthcare.com/media/62902/product%20literature_hme%20and%20moisture%20exchangers%20and%20filters_.pdf.
Intersurgical Heat and Moisture Exchangers Na http://www.intersurgical.com/products/heat-and-moisture-exchangers.
Smiths Medical Filtered Heat Moisture Exchanger 1 Ea NA http://namireto.info/smiths-medical-filtered-heat-moisture-exchanger-1-ea.asp.
Ningbo Tianhou Import and Export Co., Ltd NA http://www.tenhoo-med.com/products/Heat-Moisture-Exchanger-284977.html.
Thermotrach Heat & Moisture Exchanger NA http://www.flexicare.com/en/products/breathing-filters/thermotrach-heat--moistureexchanger.aspx.
A-M System NA http://www.a-msystems.com/p-21-heat-and-moisture-exchange-hme-filter.aspx.
Smiths Medical NA http://www.smiths-medical.com/catalog/humidification-systems/passive-humidificationsystems/thermovent-heat-moisture-exchangers1/quot-thermovent-t-quot.html.
Filter Heat Moisture Exchanger Hme, Flexlife 15F/15M, 1 Ea NA http://www.imed.com/p/Filter-Heat-Moisture-Exchanger-HME-Flexlife-15f-15m-1-ea/165277.html?utm_source=sas&utm_medium=aff&utm_campaign=product&zmam=1000941&zmas=21&zmac=180&zmap=165277.
Ballard Medical Products Ballard Flex Heat Moisture Exchange With Filter Blue 1 Ea NA http://halfusab.info/ballard-medical-products-ballard-flex-heat-moisture-exchange-withfilter-blue-1-ea.aspx.
Pharma Systems NA http://www.pharmasystems-ps.com/en/products/heat-and-moisturesexchangers/pharma-neo This Is no Longer an Active Link.
Medicomp NA http://medicompmedical.com/filters.html This Is no Longer an Active Link.
Heat and Moisture Exchange Devices: Are They Doing What They Are Supposed to Do? Lemmens HJ, Brock-Utne JG. Anesth Analg. Feb. 2004;98(2):382-5, table of contents.
The Effects of the Heat and Moisture Exchanger on Humidity, Airway Temperature, and Core Body Temperature Mary A. Delventhal; http://www.stormingmedia.us/21/2121/A212124.html.
Grea Medical Supplies NA http://www.greatmedicalsupplies.com/supply~Smiths+Medical+-+Portex+(SF)~thermovent-tportex-heatmoisture-exchange-50ca-570016.htm Unable to Retreive This Page.
Heat and Moisture Exchangers in Artificial Ventilation: An Experimental Study of the Effect of Gas Leakage S. E. Tilling and B. Hayes Br. J. Anaesth. (1987) 59(9): 1181-1188.

(56) References Cited

OTHER PUBLICATIONS

The Effect of a Newly Developed Heat and Moisture Exchanger for Pulmonary Rehabilitation of Laryngectomized Patients on the Endotracheal Temperature and Humidity. Scheenstra R, Muller S, Vincent A, Ackerstaff A, Jacobi I, Hilgers F. Respir Care. Jan. 27, 2011.

Endotracheal Temperature and Humidity in Laryngectomized Patients in a Warm and Dry Environment and the Effect of a Heat and Moisture Exchanger. Scheenstra RJ, Muller SH, Hilgers FJ. Head Neck. Oct. 27, 2010.

In Vitro Evaluation of an Active Heat-And-Moisture Exchanger: The Hygrovent Gold. Pelosi P, Severgnini P, Selmo G, Corradini M, Chiaranda M, Novario R, Park GR. Respir Care. Apr. 2010;55(4):460-6.

Humidification and Secretion Volume in Mechanically Ventilated Patients. Solomita M, Palmer LB, Daroowalla F, Liu J, Miller D, LeBlanc DS, Smaldone GC. Respir Care. Oct. 2009;54(10):1329-35.

Pulmonary Rehabilitation After Total Laryngectomy Using a Heat and Moisture Exchanger (Hme)]. Lorenz KJ, Maier H. Laryngorhinootologie. Aug. 2009;88(8):513-22. Epub Jul. 30, 2009.

The Effect of a Heat and Moisture Exchanger (Provox Hme) on Pulmonary Protection After Total Laryngectomy: A Randomized Controlled Study Bie_ S, Okla S, van As-Brooks CJ, Ackerstaff AH. Eur Arch Otorhinolaryngol. Mar. 2010;267(3):429-35.

The Influence of a Heat and Moisture Exchanger on Tracheal Climate in a Cold Environment. Zuur JK, Muller SH, Vincent A, Sinaasappel M, de Jongh FH, Hilgers FJ. Med Eng Phys. Sep. 2009;31(7):852-7. Epub May 28, 2009.

Water Content of Delivered Gases During Non-Invasive Ventilation in Healthy Subjects. Lellouche F, Maggiore SM, Lyazidi A, Deye N, Taillé S, Brochard L. Intensive Care Med. Jun. 2009;35(6):987-95. Epub Mar. 18, 2009.

Prospective Controlled Study of Microbial Colonization of the Trachea in Tracheotomized and Laryngectomized Patients With Hme (Heat and Moisture Exchanger) Kramp B, Donat M, Dommerich S, Pau HW, Podbielski A. Acta Otolaryngol. Oct. 2009;129(10):1136-44.

Heat and Moisture Exchanger: Importance of Humidification in Anaesthesia and Ventilatory Breathing System. Parmar V. J Indian Med Assoc. Aug. 2008;106(8):533-5, 537.

Tracheostoma Humidifier: Influence on Secretion and Voice of Patients With Total Laryngectomy. Masson AC, Fouquet ML, Gonçalves AJ. Pro Fono. Jul.-Sep. 2008;20(3):183-9.

Comparison of Two Humidification Systems for Long-Term Non-invasive Mechanical Ventilation. Nava S, Cirio S, Fanfulla F, Carlucci A, Navarra A, Negri A, Ceriana P. Eur Respir J. Aug. 2008;32(2):460-4.

Ventilator-Associated Pneumonia in Adults in Developing Countries: A Systematic Review. Arabi Y, Al-Shirawi N, Memish Z, Anzueto A. Int J Infect Dis. Sep. 2008;12(5):505-12.

The Effect of Heat-Moisture Exchanger and Closed-Circuit Technique on Airway Climate During Desflurane Anesthesia. Lu CC, Ho ST, Liaw WJ, Chen RM, Chen TL, Lin CY. J Anesth. 2008;22(1):7-12. Epub Feb. 27, 2008.

Montreal'S Experience With Cyranose Heat and Moisture Exchanger Use in 15 Laryngectomized Patients. Dupuis P, Guertin L, Rainville MS, Prud'homme DL, Lavigne F. J Otolaryngol. Aug. 2007;36(4):208-12.

Secretion Management in the Mechanically Ventilated Patient. Branson RD. Respir Care. Oct. 2007;52(10):1328-42; discussion 1342-7.

Moisturizing and Mechanical Characteristics of a New Counter-Flow Type Heated Humidifier. Schumann S, Stahl CA, Möller K, Priebe HJ, Guttmann J. Br J Anaesth. Apr. 2007;98(4):531-8. Epub Feb. 27, 2007.

Efficacy of a Heat and Moisture Exchanger in Inhalation Anesthesia At Two Different Flow Rates. Yamashita K, Yokoyama T, Abe H, Nishiyama T, Manabe M. J Anesth. 2007;21(1):55-8. Epub Jan. 30, 2007.

The Effects of Apparatus Dead Space on P(Aco2) In Patients Receiving Lung-Protective Ventilation. Hinkson CR, Benson MS, Stephens LM, Deem S. Respir Care. Oct. 2006;51(10):1140-4.

Effect of Humidifying Devices on the Measurement of Tidal Volume by Mechanical Ventilators. Fujita Y, Imanaka H, Fujino Y, Takeuchi M, Tomita T, Mashimo T, Nishimura M. J Anesth. 2006;20(3):166-72.

Effect of Heat and Moisture Exchanger (Hme) Positioning on Inspiratory Gas Humidification. Inui D, Oto J, Nishimura M. BMC Pulm Med. Aug. 8, 2006;6:19.

Ventilator-Associated Pneumonia Using a Heated Humidifier or a Heat and Moisture Exchanger: A Randomized Controlled Trial [Isrctn88724583] Lorente L, Lecuona M, Jiménez A, Mora ML, Sierra A. Crit Care. 2006;10(4):R116.

Under-Humidification and Over-Humidification During Moderate Induced Hypothermia With Usual Devices. Lellouche F, Qader S, Taille S, Lyazidi A, Brochard L. Intensive Care Med. Jul. 2006;32(7):1014-21.

[Intensive Care Medicine—Update 2005]. Flohé S, Lendemans S, Schmitz D, Waydhas C. Zentralbl Chir. Jun. 2006;131(3):175-87.

Effect of Ventilation Equipment on Imposed Work of Breathing. French CJ, Bellomo R, Buckmaster J. Crit Care Resusc. Sep. 2001;3(3):148-52.

Double-Heater-Wire Circuits and Heat-And-Moisture Exchangers and the Risk of Ventilator-Associated Pneumonia. Boots RJ, George N, Faoagali JL, Druery J, Dean K, Heller RF. Crit Care Med. Mar. 2006;34(3):687-93.

Influence of Passive Humidification on Respiratory Heat Loss in Tracheotomized Patients. Rozsasi A, Leiacker R, Fischer Y, Keck T. Head Neck. Jul. 2006;28(7):609-13.

Partial Liquid Ventilation: Effects of Closed Breathing Systems, Heat-And-Moisture-Exchangers and Sodalime Absorbers on Perfluorocarbon Evaporation. Wilms CT, Schober P, Kalb R, Loer SA. Eur J Anaesthesiol. Jan. 2006;23(1):31-5.

Bench-To-Bedside Review: Adjuncts to Mechanical Ventilation in Patients With Acute Lung Injury. Rouby JJ, Lu Q. Crit Care. Oct. 5, 2005;9(5):465-71. Epub Jun. 28, 2005.

Prolonged Sedation in the Pediatric Intensive Care Unit May Be Difficult Because of Tolerance, Drug Dependence and Withdrawal, Drug Interactions and Unwanted Drug Effects. We Present Three Patients Sedated With Isoflurane Via the Anesthetic Conserving Dev Sackey PV, Martling CR, Radell PJ. Paediatr Anaesth. Oct. 2005;15(10):879-85.

Comparison of the Bain System and Uniflow Universal Anaesthetic Breathing Systems in Spontaneously Breathing Young Pigs. Almubarak A, Clarke K, Jackson TL. Vet Anaesth Analg. Sep. 2005;32(5):314-21.

Compliance, Quality of Life and Quantitative Voice Quality Aspects of Hands-Free Speech. Op de Coul BM, Ackerstaff AH, van As-Brooks CJ, van den Hoogen FJ, Meeuwis CA, Manni JJ, Hilgers FJ. Acta Otolaryngol. Jun. 2005;125(6):629-37.

Volume-Guaranteed Pressure-Support Ventilation Facing Acute Changes in Ventilatory Demand. Jaber S, Delay JM, Matecki S, Sebbane M, Eledjam JJ, Brochard.

Inhalational Anaesthetics in the Icu: Theory and Practice of Inhalational Sedation in the Icu, Economics, Risk-Benefit. Meiser A, Laubenthal H. Best Pract Res Clin Anaesthesiol. Sep. 2005;19(3):523-38.

Tracheal Climate in Laryngectomees After Use of a Heat and Moisture Exchanger. Keck T, Dürr J, Leiacker R, Rettinger G, Rozsasi A. Laryngoscope. Mar. 2005;115(3):534-7.

Periodically Changing Ventilator Circuits Is Not Necessary to Prevent Ventilator-Associated Pneumonia When a Heat and Moisture Exchanger Is Used. Lorente L, Lecuona M, Galván R, Ramos MJ, Mora ML, Sierra A. Infect Control Hosp Epidemiol. Dec. 2004;25(12):1077-82.

International Search Report and Written Opinion for PCT/US2014/24813; dated Mar. 20, 2015.

\* cited by examiner

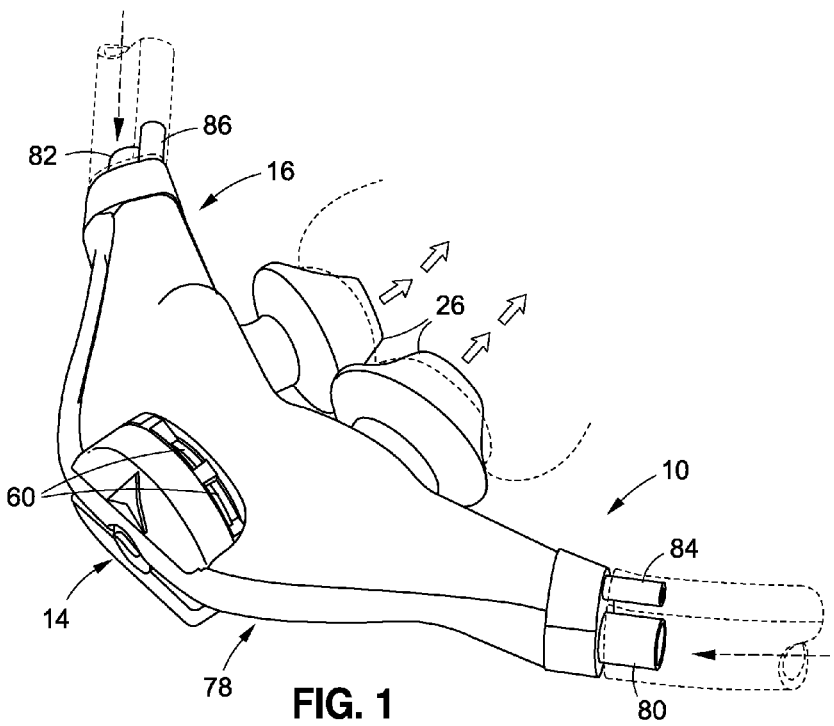
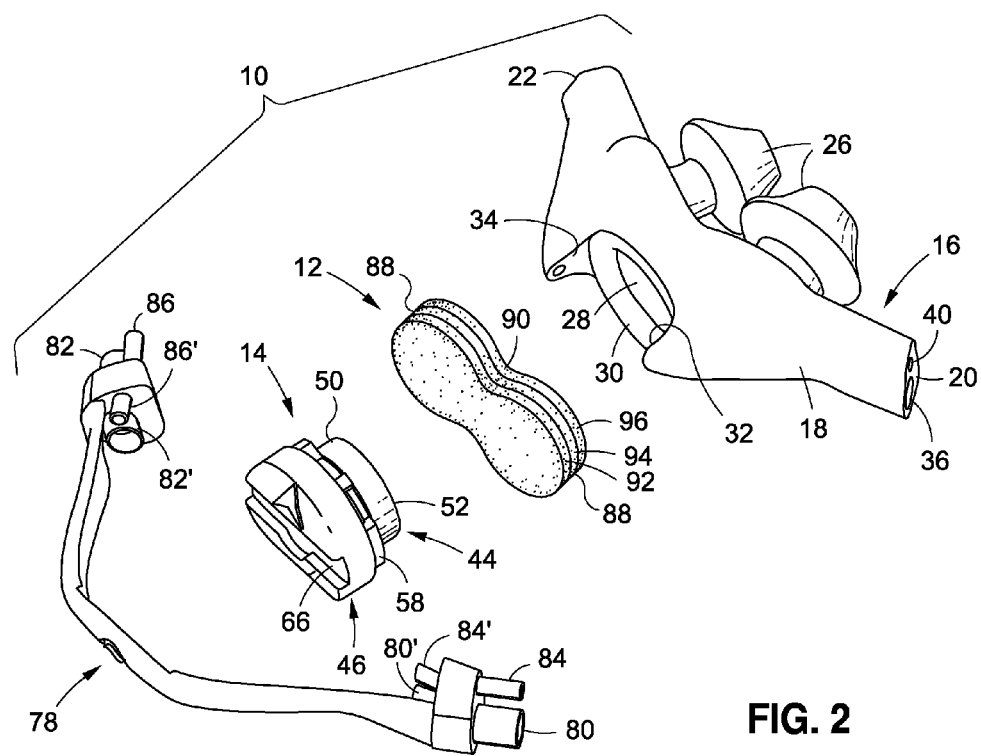

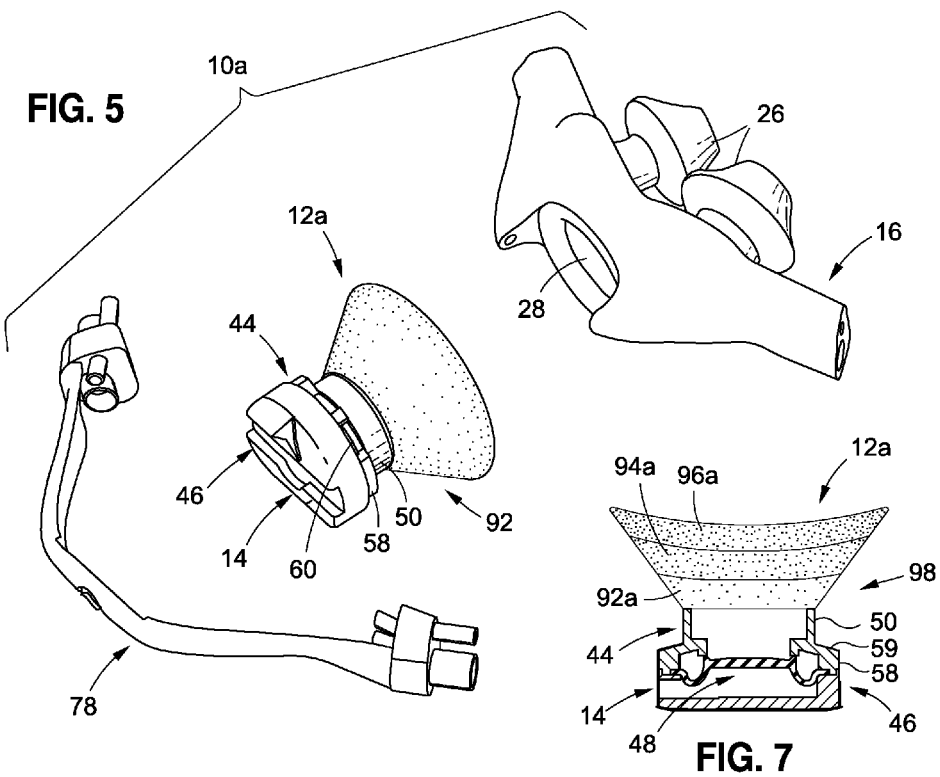
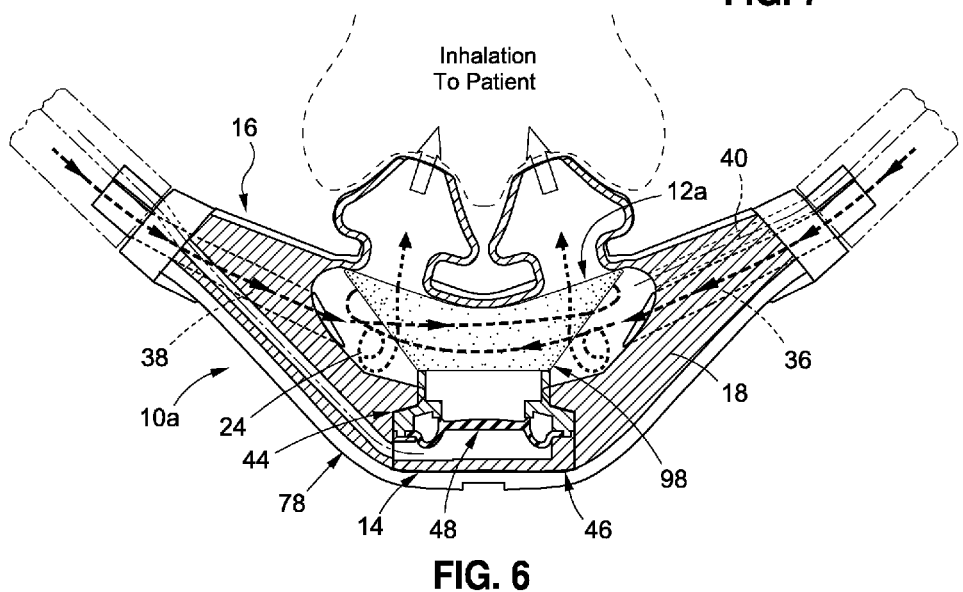

VENTILATION MASK WITH HEAT AND MOISTURE EXCHANGE DEVICE

CROSS-REFERENCE TO RELATED APPLICATIONS

Not Applicable

STATEMENT RE: FEDERALLY SPONSORED RESEARCH/DEVELOPMENT

Not Applicable

BACKGROUND OF THE INVENTION

1. Field of the Invention

The present invention relates to systems and methods for controlling delivery of a pressurized flow of breathable gas to a patient and, more particularly, to a ventilation mask such as nasal mask, nasal prongs mask or nasal pillows mask for use in critical care ventilation, respiratory insufficiency or OSA (obstructive sleep apnea) with CPAP (Continuous Positive Airway Pressure) therapy and incorporating a heat and moisture exchange device which is uniquely configured to maximize the transmission of heat and moisture to and from air flowing through the ventilation mask.

2. Description of the Related Art

The use of ventilator and breathing circuits to provide respiratory assistance to a patient is well known in the medical arts. The ventilator and breathing circuit provides mechanical assistance to patients who are having difficulty breathing on their own. In certain types of breathing circuits, a ventilator unit or flow generator is fluidly connected to a ventilation mask worn by the patient. Such fluid connection is typically achieved through the use of ventilation tubing or a tubing circuit which is operative to deliver the ventilation gas from the flow generator to the patient via the mask worn by the patient.

In normal, unassisted respiration, heat and moisture are absorbed from the exhaled air by the inner walls of the oral and nasal cavities of the patient as the air travels from the patient's lungs to the outside environment. This heat and moisture is then transferred to the inhaled air in the next breath, helping to keep the mucus membranes of the patient's lungs humidified and at the proper temperature. Mechanical ventilation bypasses this natural system, often resulting in dry air of incorrect temperature being introduced into the oral and nasal cavities, and hence the lungs of the patient. After a period of time, the respiratory tract of the ventilated patient becomes dried, often causing discomfort. Thus, one of the known disadvantages of conventional breathing circuits is that the air delivered to the patient's lungs is not at the appropriate humidity and/or temperature level.

In order to provide for proper humidity and temperature of the air in ventilator and breathing circuits, it is known to integrate a heat and moisture exchange (HME) device into the breathing circuit. Typically, HME devices are placed into the breathing circuit somewhere within the flow path of the warm, moist air which is exhaled by the patient. The exhaled air enters the HME device, where the moisture and heat are absorbed by those materials used to fabricate the same. These materials then impart the absorbed heat and moisture to the inhaled air in the next breath. The retention of warmth and high humidity helps to prevent the patient's lungs and mucus layers from drying out. Currently known HME devices generally consist of a housing that contains a layer of flexible, fibrous, gas-permeable media or material. As indicated above, this media has the capacity to retain moisture and heat from the air that is exhaled from the patient's lungs, and then transfer the captured moisture and heat to the inhaled air when the patient is inhaling with the assistance of the flow generator. The fibrous material or media in the HME device may be made of foam or paper or other suitable materials that are untreated or treated with hygroscopic material.

However, currently known HME devices possess certain deficiencies which detract from their overall utility. More particularly, the structural attributes of currently known HME devices does not make them particularly well suited for integration into ventilation masks such as nasal prongs or nasal pillows masks. In this regard, nasal pillows masks typically comprise a housing or cushion, the size of which is adapted to allow it to be positioned below the patient's nostrils and above the patient's mouth. The resultant relatively small size or profile of the cushion does not lend itself to the easy integration of conventional HME devices directly therein. Rather, such HME devices must typically be located within the tubing circuit proximate, but not directly within, the cushion. As will be recognized, the integration of the HME device within the cushion immediately adjacent the patient's nostrils would optimize the ability of such HME device to facilitate the desired heat and moisture exchange operation with air inhaled and exhaled by a patient wearing the corresponding nasal pillows mask. The present invention addresses this issue by providing a ventilation mask such as a nasal pillows mask wherein an HME device is directly integrated into the housing or cushion thereof (thus residing in extremely close proximity to the patient's nostrils), and is further uniquely configured to induce a flow pattern between it and the cushion which maximizes the transmission of heat and moisture to air which is inhaled by and exhaled from the patient through the nasal pillows mask. These, as well as other features and advantages of the present invention will be described in more detail below.

BRIEF SUMMARY OF THE INVENTION

In accordance with the present invention, there is provided a ventilation mask (e.g., a nasal pillows mask) for achieving positive pressure mechanical ventilation (inclusive of CPAP, ventilatory support, critical care ventilation, emergency applications). The mask preferably includes a pressure sensing modality proximal to the patient connection. Such pressure sensing modality may be a pneumatic port with tubing that allows transmission of the patient pressure back to the ventilator for measurement, or may include a transducer within the mask. The pressure sensing port is used in the system to allow pressure sensing for achieving and/or monitoring the therapeutic pressures. Alternately or additionally, the mask may include a flow sensing modality located therewithin for achieving and/or monitoring the therapeutic flows.

The mask of the present invention also includes a piloted exhalation valve that is used to achieve the target pressures/flows to the patient. In the preferred embodiment, the pilot for the valve is pneumatic and driven from the gas supply tubing from the ventilator. The pilot can also be a preset pressure derived in the mask, a separate pneumatic line from the ventilator, or an electro-mechanical control. In accordance with the present invention, the valve is preferably implemented with a diaphragm.

The mask of the present invention further includes a heat and moisture exchange (HME) device which is integrated therein. The HME device can fully or at least partially replace a humidifier (cold or heated pass-over; active or passive) which may otherwise be included in the ventilation system employing the use of the mask. The HME device is positioned within the mask so as to be able to intercept the flow delivered from a flow generator to the patient in order to humidify it, and further to intercept the exhaled flow of the patient in order to capture humidity and heat for the next breath. The HME device can also be used as a structural member of the mask, adding a cushioning effect and simplifying the design of the cushion thereof.

The present invention is best understood by reference to the following detailed description when read in conjunction with the accompanying drawings.

BRIEF DESCRIPTION OF THE DRAWINGS

These, as well as other features of the present invention, will become more apparent upon reference to the drawings wherein:

FIG. 1 is top perspective view of a nasal pillows mask constructed in accordance with a first embodiment of the present invention and including a heat and moisture exchange device integrated into the cushion thereof;

FIG. 2 is an exploded view of the nasal pillows mask shown in FIG. 1;

FIG. 5 is an exploded view of a nasal pillows mask constructed in accordance with a second embodiment of the present invention and including a sub-assembly comprising a heat and moisture exchange device and a piloted exhalation valve;

FIG. 6 is a partial cross-sectional view of the nasal pillows mask shown in FIG. 5, further depicting the flow pattern through the cushion of the mask and the heat and moisture exchange device of the sub-assembly disposed therein during an inhalation phase of a patient wearing the mask;

FIG. 7 is a side-elevational view of the sub-assembly comprising the heat and moisture exchange device and piloted exhalation valve as shown in FIG. 5;

Common reference numerals are used throughout the drawings and detailed description to indicate like elements.

DETAILED DESCRIPTION OF THE INVENTION

Figure 3:
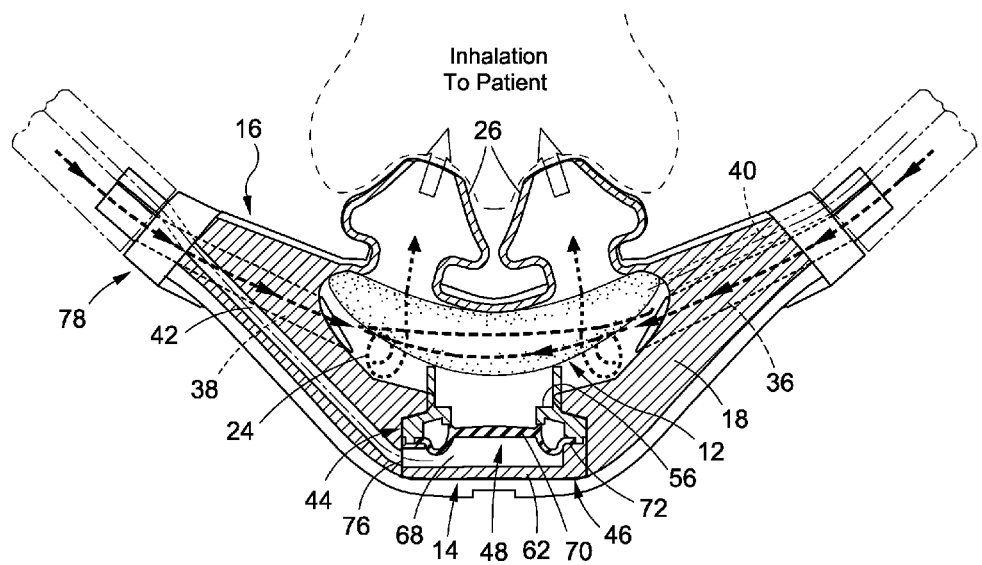
FIG. 3 is a partial cross-sectional view of the nasal pillows mask shown in FIG. 1, further depicting the flow pattern through the cushion of the mask and the heat and moisture exchange device disposed therein during an inhalation phase of a patient wearing the mask.

Referring now to the drawings wherein the showings are for purposes of illustrating various embodiments of the present invention only, and not for purposes of limiting the same, FIGS. 1-4 depict a ventilation mask 10 (e.g., a nasal pillows mask) which is constructed in accordance with a first embodiment of the present invention and has a heat and moisture exchange (HME) device 12 integrated therein. Though the mask 10 is depicted as a nasal pillows mask, it is contemplated that that the HME device 12, as will be described in more detail below, may be integrated into other types ventilation masks, such as nasal prongs masks, nasal masks, full face masks and oronasal masks. The mask 10 includes an integrated, diaphragm-implemented, piloted exhalation valve 14, the structural and functional attributes of which will be described in more detail below as well.

Figure 4:
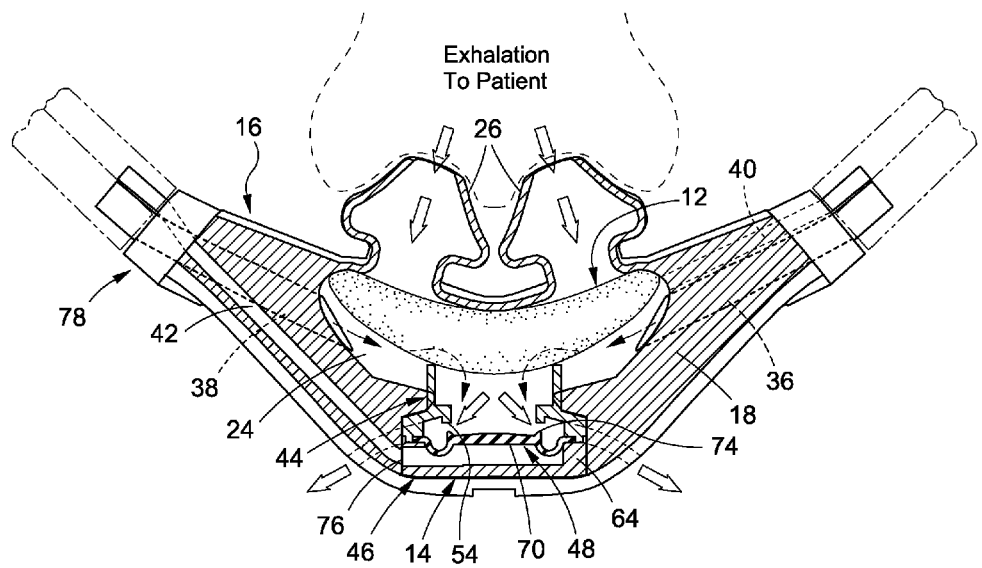
FIG. 4 is a partial cross-sectional view of the nasal pillows mask shown in FIG. 1, further depicting the flow pattern through the cushion of the mask and the heat and moisture exchange device disposed therein during an exhalation phase of a patient wearing the mask.

The mask 10 comprises a housing or cushion 16. The cushion 16, which is preferably fabricated from a silicone elastomer having a Shore A hardness in the range of from about 20 to 60 and preferably about 40, is formed as a single, unitary component, and is shown individually in FIG. 2. The cushion 16 includes a main body portion 18 which defines a first outer end surface 20 and an opposed second outer end surface 22. The main body portion 18 further defines an interior fluid chamber 24 which is of a prescribed shape and volume. In addition to the main body portion 18, the cushion 16 includes an identically configured pair of hollow pillow portions 26 which protrude from the main body portion 18 in a common direction and in a prescribed spatial relationship relative to each other. More particularly, in the cushion 16, the spacing between the pillow portions 26 is selected to facilitate the general alignment thereof with the nostrils of an adult patient when the mask 10 is worn by such patient. As seen in FIGS. 3 and 4, each of the pillow portions 26 fluidly communicates with the fluid chamber 24.

As shown in FIG. 2, the main body portion 18 of the cushion 16 includes an enlarged, circularly configured valve opening 28 which is in direct fluid communication with the fluid chamber 24. The valve opening 28 is positioned in generally opposed relation to the pillow portions 26 of the cushion 16, and is circumscribed by an annular valve seat 30 also defined by the main body portion 18. As also shown in FIG. 2, the main body portion 18 further defines opposed first and second inner end surfaces 32, 34 which protrude outwardly from the periphery of the valve opening 28, and are diametrically opposed relative thereto so as to be spaced by an interval of approximately 180°. The valve opening 28, valve seat 30, and first and second inner end surfaces 32, 34 are adapted to accommodate the exhalation valve 14 of the mask 10 in a manner which will be described in more detail below.

The main body portion 18 of the cushion 16 further defines first and second gas delivery lumens 36, 38 which extend from respective ones of the first and second outer end surfaces 20, 22 into fluid communication with the fluid chamber 24. Additionally, a pressure sensing lumen 40 defined by the main body portion 18 extends from the first outer end surface 20 into fluid communication with the fluid chamber 24. The main body portion 18 further defines a valve pilot lumen 42 which extends between the second outer end surface 22 and the second inner end surface 34. The use of the first and second gas delivery lumens 36, 38, the pressure sensing lumen 40, and the valve pilot lumen 42 will also be discussed in more detail below. Those of ordinary skill in the art will recognize that the gas delivery lumens 36, 38 may be substituted with a single gas delivery lumen and/or positioned within the cushion 16 in orientations other than those depicted in FIGS. 4 and 5. For example, the gas delivery lumen(s) of the cushion 16 may be positioned frontally, pointing upwardly, pointing downwardly, etc. rather than extending laterally as shown in FIGS. 4 and 5.

The exhalation valve 14 of the mask 10 is made of three (3) primary parts or components, and more particularly a seat member 44, a cap member 46, and a diaphragm 48 which is operatively captured between the seat and cap members 44, 46. The seat and cap members 44, 46 are each preferably fabricated from a plastic material, with the diaphragm 48 preferably being fabricated from an elastomer having a Shore A hardness in the range of from about 20-40. The detailed structural and functional attributes of the exhalation valve 14 are described with particularity in Applicant's co-pending U.S. patent application Ser. No. 13/411, 348 entitled VENTILATION MASK WITH INTEGRATED PILOTED EXHALATION VALVE filed Mar. 2, 2012, now issued as U.S. Pat. No. 8,844,533, the disclosure of which is incorporated herein by reference.

The seat member 44 includes a tubular, generally cylindrical wall portion 50 which defines a distal, annular outer rim 52 and an opposed annular inner seating surface 54. As shown in FIG. 4, the diameter of the outer rim 52 exceeds that of the seating surface 54. Along these lines, the inner surface of the wall portion 50 is not of a uniform inner diameter, but rather is segregated into first and second inner surface sections which are of differing inner diameters, and separated by an annular shoulder 56. In addition to the wall portion 50, the seat member 44 includes an annular flange portion 58 which protrudes radially from that end of the wall portion 50 opposite the outer rim 52. The flange portion 58 includes a plurality of exhaust vents 60 which are located about the periphery thereof in a prescribed arrangement and spacing relative to each other. The seat member 44 is formed such that each of the exhaust vents 60 normally fluidly communicates with the bore or fluid conduit defined by the wall portion 50.

The cap member 46 of the exhaust valve 14 comprises a circularly configured base portion 62 which defines an inner surface and an opposed outer surface. In addition to the base portion 62, the cap member 46 includes an annular flange portion 64 which circumvents and protrudes generally perpendicularly relative to the inner surface of the base portion 62. The flange portion 64 defines a distal annular shoulder. The distal shoulder of the flange portion 64 and the inner surface of the base portion 62 extend along respective ones of a spaced, generally parallel pair of planes. Formed in the outer surface of the base portion 62 is an elongate groove 66 which extends diametrically across such outer surface. The use of the groove 66 will be described in more detail below. The seat and cap members 44, 46, when attached to each other in the fully assembled exhalation valve 14, collectively define an interior valve chamber 68 of the exhalation valve 14. More particularly, such valve chamber 68 is generally located between the inner surface defined by the base portion 62 of the cap member 46 and the seating surface 54 defined by the wall portion 50 of the seat member 44.

The diaphragm 48 of the exhalation valve 14, which resides within the valve chamber 68, has a circularly configured, central body portion 70, and a peripheral flange portion 72 which is integrally connected to and circumvents the body portion 70. The body portion 70 includes an annular lip 74 which circumvents and protrudes upwardly from one side or face thereof. The flange portion 72 includes an arcuately contoured primary region and a distal region which protrudes radially from the primary region. As such, the primary region of the flange portion 72 extends between the distal region thereof and the body portion 70, and defines a continuous, generally concave channel.

In the exhalation valve 14, the flange portion 72 of the diaphragm 48 is operatively captured between the flange portions 58, 64 of the seat and cap members 44, 46. More particularly, the annular distal region of the flange portion 72 is compressed (and thus captured) between the shoulder defined by the flange portion 64 of the cap member 46, and a complimentary annular shoulder which is defined by the flange portion 58 of the seat member 44 proximate the exhaust vents 60. The orientation of the diaphragm 48 within the valve chamber 68 when captured between the seat and cap members 44, 46 is such that the channel defined by the arcuately contoured primary region of the flange portion 72 is directed toward or faces the seating surface 54 defined by the wall portion 50 of the seat member 44.

The diaphragm 48 (and hence the exhalation valve 14) is selectively moveable between an open position (shown in FIG. 4) and a closed position (shown in FIG. 3). When in its normal, open position, the diaphragm 48 is in a relaxed, unbiased state. Importantly, in either of its open or closed positions, the diaphragm 48 is not normally seated directly against the inner surface defined by the base portion 62 of the cap member 46. Rather, a gap is normally maintained between the body portion 70 of the diaphragm 48 and the inner surface of the base portion 62. The width of such gap when the diaphragm 48 is in its open position is generally equal to the fixed distance separating the inner surface of the base portion 62 from the distal shoulder of the flange portion 64. Further, when the diaphragm 48 is in its open position, the body portion 70, and in particular the lip 74 protruding therefrom, is itself disposed in spaced relation to the seating surface 54 defined by the wall portion 50 of the seat member 44. As such, when the diaphragm 48 is in its open position, fluid is able to freely pass through the fluid conduit defined by the wall portion 50, between the seating surface 54 and diaphragm 48, and through the exhaust vents 60 to ambient air. The flange portion 64 of the cap member 46 is further provided with a pilot port 76 which extends therethrough and, in the fully assembled exhalation valve 14, fluidly communicates with that portion of the valve chamber 68 disposed between the body portion 70 of the diaphragm 48 and the inner surface of the base portion 62 of the cap member 46. The use of the pilot port 76 will also be described in more detail below.

In the exhalation valve 14, the diaphragm 48 is resiliently deformable from its open position (to which it may be normally biased) to its closed position. Since the diaphragm 48 is normally biased to its open position, it provides a failsafe to allow a patient to inhale ambient air through the exhalation valve 14 and exhale ambient air therethrough (via the exhaust vents 60) during any ventilator malfunction or when the mask 10 is worn without the therapy being delivered by the ventilator. When the diaphragm 48 is moved or actuated to its closed position, the lip 74 of the body portion 70 is firmly seated against the seating surface 54 defined by the wall portion 50 of the seat member 44. The seating of the lip 74 against the seating surface 54 effectively blocks fluid communication between the fluid conduit defined by the wall portion 50 and the valve chamber 68 (and hence the exhaust vents 60 which fluidly communicate with the valve chamber 68).

In the mask 10, the cooperative engagement between the exhalation valve 14 and the cushion 16 is facilitated by the advancement of the wall portion 50 of the seat member 44 into the valve opening 28 defined by the cushion 16. Such advancement is limited by the ultimate abutment or engagement of a beveled seating surface defined by the flange portion 58 of the seat member 44 against the complimentary valve seat 30 of the cushion 16 circumventing the valve opening 28. Upon the engagement of such seating surface of the flange portion 58 to the valve seat 30, the fluid chamber 24 of the cushion 16 fluidly communicates with the fluid conduit defined by the wall portion 50 of the seat member 44. As will be recognized, if the diaphragm 48 resides in its normal, open position, the fluid chamber 24 is further placed into fluid communication with the valve chamber 68 via the fluid conduit defined by the wall portion 50, neither end of which is blocked or obstructed by virtue of the gap defined between the lip 74 of the diaphragm 48 and the seating surface 54 of the wall portion 50.

When the exhalation valve 14 is operatively coupled to the cushion 16, in addition to the valve seat 30 being seated against the beveled seating surface 59 of the flange portion 58 of the seat member 44, the first and second inner end surfaces 32, 34 of the cushion 16 are seated against respective, diametrically opposed sections of the flange portion 64 defined by the cap member 46. The orientation of the exhalation valve 14 relative to the cushion 16 is such that the end of the valve pilot lumen 42 extending to the second inner end surface 34 is aligned and fluidly communicates with the pilot port 76 within the flange portion 64 of the cap member 46. As such, in the mask 10, the valve pilot lumen 42 is in continuous, fluid communication with that portion of the valve chamber 68 defined between the inner surface of the base portion 62 of the cap member 46, and the body portion 70 of the diaphragm 48.

To assist in maintaining the cooperative engagement between the exhalation valve 14 and the cushion 16, the mask 10 is further preferably provided with an elongate frame member 78. The frame member 78 has a generally V-shaped configuration, with a central portion thereof being accommodated by and secured within the complimentary groove 66 formed in the outer surface defined by the base portion 62 of the cap member 46. The opposed end portions of the frame member 78 are cooperatively engaged to respective ones of the first and second outer end surfaces 20, 22 of the cushion 16. More particularly, as shown in FIG. 2, the frame member 78 includes an identically configured pair of first and second connectors 80, 82 which extend from respective ones of the opposed end portions thereof. The first and second connectors 80, 82 each define opposed inner and outer portions which have generally cylindrical, tubular configurations. The inner portion 80' of the first connector 80 is advanced into and frictionally retained within the first gas delivery lumen 36 of the cushion 16. Similarly, the inner portion 82' of the second connector 82 is advanced into and frictionally retained within the second gas delivery lumen 38 of the cushion 16. As will be described in more detail below, the outer portions of the first and second connectors 80, 82 of the frame member 78 are each adapted to be advanced into and frictionally retained within a corresponding lumen of a respective one of a pair of bi-lumen tubes fluidly coupled to the mask 10.

The frame member 78 further includes a pressure port 84 which is disposed adjacent the first connector 80. Like each of the first and second connectors 80, 82, the pressure port 84 defines opposed inner and outer portions which each have a generally cylindrical, tubular configuration. The inner portion 84' of the pressure port 84 is aligned and fluidly communicates with the pressure sensing lumen 40 of the cushion 16 subsequent to being advanced and frictionally maintained therein. The frame member 78 is also provided with a pilot port 86 which is disposed adjacent the second connector 82 and also defines opposed inner and outer portions which each have a generally cylindrical, tubular configuration. The inner portion 86' of the pilot port 86 is aligned and fluidly communicates with the valve pilot lumen 42 of the cushion 16 subsequent to being advanced and frictionally maintained therein. The outer portions of the pressure and pilot ports 84, 86 of the frame member 78 are adapted to be advanced into and frictionally maintained within corresponding lumens of respective ones of the aforementioned pair of bi-lumen tubes which are fluidly connected to the mask 10 within a ventilation system incorporating the same. The receipt of the frame member 78 within the groove 66 of the cap member 46 ensures that the cushion 16, the exhalation valve 14 and the frame member 78 are properly aligned, and prevents relative movement therebetween. Though not shown, it is contemplated that in one potential variation of the mask 10, the cushion 16 may be formed so as not to include the valve pilot lumen 42. Rather, a suitable valve pilot lumen would be formed directly within the frame member 78 so as to extend therein between the pilot port 86 thereof and the pilot port 76 of the exhalation valve 14.

In the mask 10, the exhalation valve 14 is piloted, with the movement of the diaphragm 48 to the closed position described above being facilitated by the introduction of positive fluid pressure into the valve chamber 68. More particularly, it is contemplated that during the inspiratory phase of the breathing cycle of a patient wearing the mask 10, the valve pilot lumen 42 will be pressurized by a pilot line fluidly coupled to the pilot port 86, with pilot pressure being introduced into that portion of the valve chamber 68 normally defined between the body portion 70 of the diaphragm 48 and the inner surface defined by the base portion 62 of the cap member 46 via the pilot port 76 extending through the flange portion 64 of the cap member 46. The fluid pressure level introduced into the aforementioned region of the valve chamber 68 via the pilot port 76 will be sufficient to facilitate the movement of the diaphragm 48 to its closed position described above.

Conversely, during the expiratory phase of the breathing cycle of the patient wearing the mask 10, it is contemplated that the discontinuation or modulation of the fluid pressure through the valve pilot lumen 42 and hence into the aforementioned region of the valve chamber 68 via the pilot port 76, coupled with the resiliency of the diaphragm 48 and/or positive pressure applied to the body portion 70 thereof, will facilitate the movement of the diaphragm 48 back to the open position or to a partially open position. In this regard, positive pressure as may be used to facilitate the movement of the diaphragm 48 to its open position may be provided by air which is exhaled from the patient during the expiratory phase of the breathing circuit and is applied to the body portion 70 via the pillows portions 26 of the cushion 16, the fluid chamber 24, and the fluid conduit defined by the wall portion 50 of the seat member 44. As will be recognized, the movement of the diaphragm 48 to the open position allows the air exhaled from the patient and entering the valve chamber 68 to be vented to ambient air after via the exhaust vents 60 within the flange portion 58 of the seat member 44 which, as indicated above, fluidly communicate with the valve chamber 68.

As will be recognized, based on the application of pilot pressure thereto, the diaphragm 48 travels from a fully open position through a partially open position to a fully closed position. In this regard, the diaphragm 48 will be partially open or partially closed during exhalation to maintain desired ventilation therapy. Further, when pilot pressure is discontinued to the diaphragm 48, it moves to an open position wherein the patient can inhale and exhale through the mask 10 with minimal restriction and with minimal carbon dioxide retention therein. This allows a patient to wear the mask 10 without ventilation therapy being applied to the mask 10. The aforementioned structural and functional features of the mask 10 also make it more comfortable to wear, and further allow it to be worn without carbon dioxide buildup, thus making it highly advantageous for the treatment of obstructive sleep apnea wherein patients complain of discomfort with ventilation therapy due to mask and pressure discomfort. When it is detected that a patient requires sleep apnea therapy, the ventilation therapy can be started (i.e., in an obstructive sleep apnea situation).

To succinctly summarize the foregoing description of the structural and functional features of the mask 10, during patient inhalation, the valve pilot lumen 42 is pressurized, which causes the diaphragm 48 to close against the seating surface 54, thus effectively isolating the fluid chamber 24 of the mask 10 from the outside ambient air. The entire flow delivered from a flow generator fluidly coupled to the mask 10 is inhaled by the patient, assuming that unintentional leaks at the interface between the cushion 16 and the patient are discarded. This functionality differs from what typically occurs in a conventional CPAP mask, where venting to ambient air is constantly open, and an intentional leak flow is continuously expelled to ambient air. During patient exhalation, the pilot pressure introduced into the valve pilot lumen 42 is controlled so that the exhaled flow from the patient can be exhausted to ambient air through the exhalation valve 14 in the aforementioned manner. In this regard, the pilot pressure is "servoed" so that the position of the diaphragm 48 relative to the seating surface 54 is modulated, hence modulating the resistance of the exhalation valve 14 to the exhaled flow and effectively ensuring that the pressure in the fluid chamber 24 of the mask 10 is maintained at a prescribed therapeutic level throughout the entire length of the exhalation phase. When the valve pilot lumen 42 is not pressurized, the exhalation valve 14 is in a normally open state, with the diaphragm 48 being spaced from the seating surface 54 in the aforementioned manner, thus allowing the patient to spontaneously breathe in and out with minimal pressure drop (also referred to as back-pressure) in the order of less than about 2 cm $H_2O$ at 60 l/min. As a result, the patient can comfortably breathe while wearing the mask 10 and while therapy is not being administered to the patient.

As indicated above, the mask 10 includes an HME device 12 which is integrated therein. More particularly, the HME device 12 is positioned within the fluid chamber 24 of the cushion 16. The HME device 12 is operative to partially or completely replace a humidifier (cold or heated pass-over; active or passive) which would otherwise be fluidly coupled to the mask 10. This is possible because the average flow through the system envisioned to be used in conjunction with the mask 10 is about half of a prior art CPAP mask, due to the absence of any intentional leak in such system.

The HME device 12 is preferably formed to have a generally hour-glass shape defining an opposed pair of enlarged end portions 88 having a reduced width, integral central portion 90 extending between the end portions 88. Prior to its advancement into the fluid chamber 24 of the cushion 16, the HME device 12 has the generally flat or planar profile shown in FIG. 2. As shown in FIGS. 3 and 4 and as will be described in more detail below, the size and shape of the HME device 12 relative to that of the fluid chamber 24 and the exhalation valve 14 partially advanced therein causes the HME device 12 to assume a generally arcuate profile when operatively positioned within the fluid chamber 24.

The HME device 12 preferably has a layered construction. More particularly, the HME device 12 is preferably fabricated to include three layers including a low density layer 92, a medium density layer 94 and a high density layer 96. The medium density layer 94 is interposed between the low and high density layers 92, 96. Those of ordinary skill in the art will recognize that the use of the three layers 92, 94, 96 to construct the HME device 12 is exemplary only, and that it may alternatively be fabricated from a single layer of material, two layers, or more than three layers without departing from the spirit and scope of the present invention.

As indicated above, the size and shape of the HME device 12 relative to the shape and internal volume of the fluid chamber 24 is selected such that the HME device 12 assumes a prescribed contour or profile when operatively positioned within the fluid chamber 24. In the mask 10, the advancement of the HME device 12 into the fluid chamber 24 occurs prior to the operative engagement of the exhalation valve 14 to the cushion 16 in the above-described manner. In this regard, prior to the cooperative engagement of the exhalation valve 14 to the cushion 16, the HME device 12 is advanced into the fluid chamber 24 via the valve opening 28 defined by the cushion 16. Though, as is apparent from FIG. 2, the size of the HME device 12 exceeds that of the valve opening 28, the pliable nature of the material(s) preferably used for the layers 92, 94, 96 of the HME device 12 allows the same to be compressed and/or folded in a manner which facilitates the advancement through the valve opening 28 and into the fluid chamber 24.

When the HME device 12 is operatively positioned within the fluid chamber 24, at least portions of the continuous peripheral side surface of the HME device 12 are abutted against corresponding regions of the interior surface of the main body portion 18 of the cushion 16 which defines the fluid chamber 24. For instance, as seen in FIGS. 3 and 4, portions of the peripheral side surface of the HME device 12 defined by each of the opposed end portions 88 thereof are abutted against corresponding interior surface regions of the main body portion 18 which are located between the inlet ends of respective ones of the first and second gas delivery lumens 36, 38, and corresponding ones of the pillow portions 26. In this regard, the size and shape of the HME device 12 is preferably such that when fully deployed within the fluid chamber 24, the HME device 12 will form a complete or substantially complete barrier between the open interiors of the pillow portions 26 and the fluid chamber 24, yet will not obstruct the inlet ends of either of the first and second gas delivery lumens 36, 38. Though not apparent from FIGS. 3 and 4, it is contemplated that the pressure sensing lumen 40 may be formed within the main body portion 18 of the cushion 16 such that the inlet end thereof which extends to the fluid chamber 24 is not covered or otherwise obstructed by the fully deployed HME device 12.

In addition to at least portions of the peripheral side surface of the HME device 12 being abutted against corresponding regions of that interior surface of the main body portion 18 defining the fluid chamber 24, it is also contemplated that a portion of the bottom surface of the HME device 12 (as viewed from the perspective shown in FIGS. 3 and 4) as defined by the low density layer 92 thereof will be abutted against the distal rim defined by the wall portion 50 of the seat member 44 upon the cooperative engagement of the exhalation valve 14 to the cushion 16. Further, as also viewed from the perspective shown in FIGS. 3 and 4, a portion of the top surface of the HME device 12 as defined by the high density layer 96 thereof is abutted against a portion of the interior surface of the main body portion 18 which is defined by that segment thereof extending between the pillow portions 26. The abutment of the opposed top and bottom surfaces of the HME device 12 against the main body portion 18 of the cushion 16 and seat member 44 of the exhalation valve 14 in the aforementioned manner, coupled with the abutment of the peripheral side surface of the HME device 12 against the main body portion 18, results in the HME device 12 assuming and being maintained in the arcuately shaped profile shown in FIGS. 3 and 4. As indicated above, when it assumes the position shown in FIGS. 3 and 4, the HME device 12 effectively segregates or separates the open interiors of the pillow portions 26 of the cushion 16 from the fluid chamber 24.

Referring again to FIG. 3, during an inhalation phase of a patient using the mask 10, air enters the fluid chamber 24 via the first and second gas delivery lumens 36, 38 which, as indicated above, are preferably unobstructed by the HME device 12. Due to the permeability of the HME device 12, the air is able to pass through the HME device 12 and into the nostrils of the patient via the pillow portions 26 of the cushion 16. This flow path is identified by the arrows shown in FIG. 3. Moisture and heat retained by the HME device 12 is transferred into the air passing therethrough prior to the air reaching the nostrils of the patient. Though air delivered into the fluid chamber 24 via the first and second gas delivery lumens 36, 38 is also capable of flowing through the HME device 12 into the exhalation valve 14, during the inhalation phase of the patient, the exhalation valve 14 is normally maintained in its closed position as described above. As a result, any gas entering the exhalation valve 14 via the HME device 12 during the inhalation phase is prevented from being vented via the exhaust vents 60 as a result of the diaphragm 48 being sealed against the seat member 44 in the aforementioned manner.

In the mask 10 having the HME device 12 positioned in the cushion 16 in the aforementioned manner, the size and shape of the HME device 12 relative to the shape and internal volume of the fluid chamber 24 is also selected such that the resultant shape of that portion of the fluid chamber 24 which is separated from the pillow portions 26 by the HME device 12 is operative to maximize flow over the exposed portions of the bottom surface of the HME device 12 defined by the low density layer 92 thereof. Such shape is also selected to impart a prescribed measure of turbulence to the air flowing into the fluid chamber 24 via the inlet ends of the first and second gas delivery lumens 36, 38. This turbulence, and the vortices resulting therefrom, assists in maximizing flow over the exposed portions of the bottom surface of the HME device 12. This in turn optimizes the level of moisture and heat transferred into the air passing through the HME device 12 and to the patient via the pillows portions 26 during the inhalation phase of the patient. An exemplary airflow pattern during the inhalation phase of the patient is shown by the arrows included in FIG. 3.

Referring again to FIG. 4, during the exhalation phase of the patient wearing the mask 10, exhaled air travels through the open interiors of the pillow portions 26 and into the exhalation valve 14 through the HME device 12. Along these lines, the material(s) preferably used to facilitate the fabrication of the HME device 12 provide for the easy passage of exhaled air through the HME device 12 and into the exhalation valve 14 without causing the patient to exert any greater exhalation force, i.e., the patient does not sense that there is an obstruction within the mask 10 during the exhalation phase. As explained above, during the exhalation phase, the diaphragm 48 of the exhalation valve 14 is actuated to its open position, thus allowing air passing through the HME device 12 and into the exhalation valve 14 to be vented to ambient via the vent ports 60 within the seat member 44 of the exhalation valve 14. As will be recognized, the HME device 12 is operative to retain moisture and heat from the air exhaled by the patient and passing therethrough during the exhalation phase, and to transfer such moisture and heat to the patient in the aforementioned manner during the inhalation phase.

It is contemplated that the HME device 12 can be permanently assembled to the cushion 16, or may alternatively be removable therefrom and thus washable and/or disposable. In this regard, the HME device 12, if removable from within the cushion 16, could be replaced on a prescribed replacement cycle. Along these lines, it is further contemplated that the HME device 12 may be impregnated with a chemical agent which facilitates a color change therein when certain conditions are satisfied indicative of a need for the replacement thereof. Additionally, it is contemplated that the HME device 12 can be used as an elastic member that adds elasticity to the cushion 16. In this regard, part of the elasticity of the cushion 16 may be attributable to its silicone construction, and further be partly attributable to the compression and deflection of the HME device 12 inside the cushion 16. Still further, it is contemplated that the HME device 12 may be infused with any one of a number of different scents which may be chosen by the patient according to preference.

Referring now to FIGS. 5 and 6, there is shown a nasal pillows mask 10a constructed in accordance with a second embodiment of the present invention. The mask 10a is substantially similar in construction to the above-described mask 10, with only the distinctions between the masks 10, 10a being highlighted below. The primary distinction between the masks 10, 10a lies in the substitution of the above-described HME device 12 of the mask 10 with an HME device 12a in the mask 10a. In the mask 10a, the HME device 12a is permanently attached to the exhalation valve 14, with the HME device 12a and the exhalation valve 14 thus collectively defining a HME subassembly 98 of the mask 10a.

The HME device 12a is preferably formed to have a generally frusto-conical shape, and preferably has a layered construction. More particularly, the HME device 12a is preferably fabricated to include three layers including a low density layer 92a, a medium density layer 94a and a high density layer 96a. The medium density layer 94a is interposed between the low and high density layers 92a, 96a. Those of ordinary skill in the art will recognize that the use of the three layers 92a, 94a, 96a to construct the HME device 12a is exemplary only, and that it may alternatively be fabricated from a single layer of material, two layers, or more than three layers without departing from the spirit and scope of the present invention. In the HME subassembly 98, a portion of the bottom surface of the HME device 12a (as viewed from the perspective shown in FIGS. 6 and 7) as defined by the low density layer 92a thereof is abutted against and permanently attached to the distal rim defined by the wall portion 50 of the seat member 44.

The size and shape of the HME device 12*a* relative to the shape and internal volume of the fluid chamber 24 is selected such that the HME device 12*a* assumes a prescribed orientation within the fluid chamber 24 when operatively positioned therein. Since the HME device 12*a* is part of the HME subassembly 98 in the mask 10*a* (i.e., is attached to the exhalation valve 14), the advancement of the HME device 12*a* into the fluid chamber 24 occurs concurrently with the process of attaching the exhalation valve 14 to the cushion 16 in the above-described manner. In this regard, the HME device 12*a* is initially advanced into the fluid chamber 24 via the valve opening 28 defined by the cushion 16, with the exhalation valve 14 thereafter being cooperatively engaged to the cushion 16. Though, as is apparent from FIG. 5, the size of the HME device 12*a* exceeds that of the valve opening 28, the pliable nature of the material(s) preferably used for the layers 92*a*, 94*a*, 96*a* of the HME device 12*a* allows the same to be compressed and/or folded in a manner which facilitates the advancement through the valve opening 28 and into the fluid chamber 24.

When viewed from the perspective shown in FIG. 6, when the HME device 12*a* is operatively positioned within the fluid chamber 24, at least a peripheral portion of the top surface of the HME device 12*a* defined by the high density layer 96*a* thereof is abutted against corresponding regions of the interior surface of the main body portion 18 of the cushion 16 which defines the fluid chamber 24. More particularly, the peripheral portion of the top surface of the HME device 12*a* is abutted against a corresponding interior surface region of the main body portion 18 which is located between the inlet ends of the first and second gas delivery lumens 36, 38 and the pillow portions 26. Further, as also viewed from the perspective shown in FIG. 6, a central portion of the top surface of the HME device 12*a* as defined by the high density layer 96*a* thereof is abutted against a portion of the interior surface of the main body portion 18 which is defined by that segment thereof extending between the pillow portions 26. In this regard, the size and shape of the HME device 12*a* is preferably such that when fully deployed within the fluid chamber 24, the HME device 12*a* will form a complete or substantially complete barrier between the open interiors of the pillow portions 26 and the fluid chamber 24, yet will not obstruct the inlet ends of either of the first and second gas delivery lumens 36, 38. As is further shown in FIG. 6, the inlet end of the pressure sensing lumen 40 which extends to the fluid chamber 24 is not covered or otherwise obstructed by the fully deployed HME device 12*a*.

As shown in FIG. 6, during an inhalation phase of a patient using the mask 10*a*, air enters the fluid chamber 24 via the first and second gas delivery lumens 36, 38 which, as indicated above, are preferably unobstructed by the HME device 12*a*. Due to the permeability of the HME device 12*a*, the air is able to pass through the HME device 12*a* and into the nostrils of the patient via the pillow portions 26 of the cushion 16. This flow path is identified by the arrows shown in FIG. 6. Moisture and heat retained by the HME device 12*a* is transferred into the air passing there through prior to the air reaching the nostrils of the patient. Though air delivered into the fluid chamber 24 via the first and second gas delivery lumens 36, 38 is also capable of flowing through the HME device 12*a* into the exhalation valve 14, during the inhalation phase of the patient, the exhalation valve 14 is normally maintained in its closed position as described above. As a result, any gas entering the exhalation valve 14 via the HME device 12*a* during the inhalation phase is prevented from being vented via the exhaust vents 60 as a result of the diaphragm 48 being sealed against the seat member 44 in the aforementioned manner.

In the mask 10*a* having the HME device 12*a* positioned in the cushion 16 in the aforementioned manner, the size and shape of the HME device 12*a* relative to the shape and internal volume of the fluid chamber 24 is also selected such that the resultant shape of that portion of the fluid chamber 24 which is separated from the pillow portions 26 by the HME device 12*a* is operative to maximize flow over the exposed portions of the bottom surface of the HME device 12*a* defined by the low density layer 92*a* thereof. Such shape is also selected to impart a prescribed measure of turbulence to the air flowing into the fluid chamber 24 via the inlet ends of the first and second gas delivery lumens 36, 38. This turbulence, and the vortices resulting therefrom, assists in maximizing flow over the exposed portions of the bottom surface of the HME device 12*a*. This in turn optimizes the level of moisture and heat transferred into the air passing through the HME device 12*a* and to the patient via the pillows portions 26 during the inhalation phase of the patient. An exemplary airflow pattern during the inhalation phase of the patient is shown by the arrows included in FIG. 6.

During the exhalation phase of the patient wearing the mask 10*a*, exhaled air travels through the open interiors of the pillow portions 26 and into the exhalation valve 14 through the HME device 12*a*. Along these lines, the material(s) preferably used to facilitate the fabrication of the HME device 12*a* provide for the easy passage of exhaled air through the HME device 12*a* and into the exhalation valve 14 without causing the patient to exert any greater exhalation force, i.e., the patient does not sense that there is an obstruction within the mask 10*a* during the exhalation phase. As explained above, during the exhalation phase, the diaphragm 48 of the exhalation valve 14 is actuated to its open position, thus allowing air passing through the HME device 12*a* and into the exhalation valve 14 to be vented to ambient via the vent ports 60 within the seat member 44 of the exhalation valve 14. As will be recognized, the HME device 12*a* is operative to retain moisture and heat from the air exhaled by the patient and passing therethrough during the exhalation phase, and to transfer such moisture and heat to the patient in the aforementioned manner during the inhalation phase.

Since the HME device 12*a* is permanently assembled to the exhalation valve 14 in the HME subassembly 98, is may be easily removed from within the fluid chamber 24 upon the detachment of the exhalation valve 14 therefrom, thus making it washable and/or replaceable. In this regard, the HME device 12*a* could be replaced on a prescribed replacement cycle. Along these lines, it is contemplated that the HME device 12*a* may be impregnated with a chemical agent which facilitates a color change therein when certain conditions are satisfied indicative of a need for the replacement thereof. It is also contemplated that the HME device 12*a* may be infused with any one of a number of different scents which may be chosen by the patient according to preference.

Figure 8:
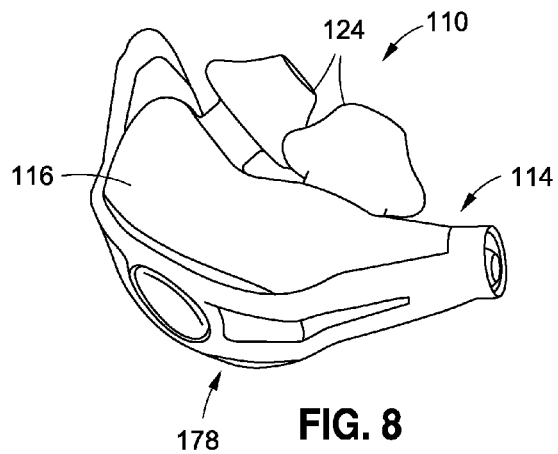
FIG. 8 is top perspective view of a nasal pillows mask constructed in accordance with a third embodiment of the present invention and including a heat and moisture exchange device integrated into the cushion thereof.
Figure 9:
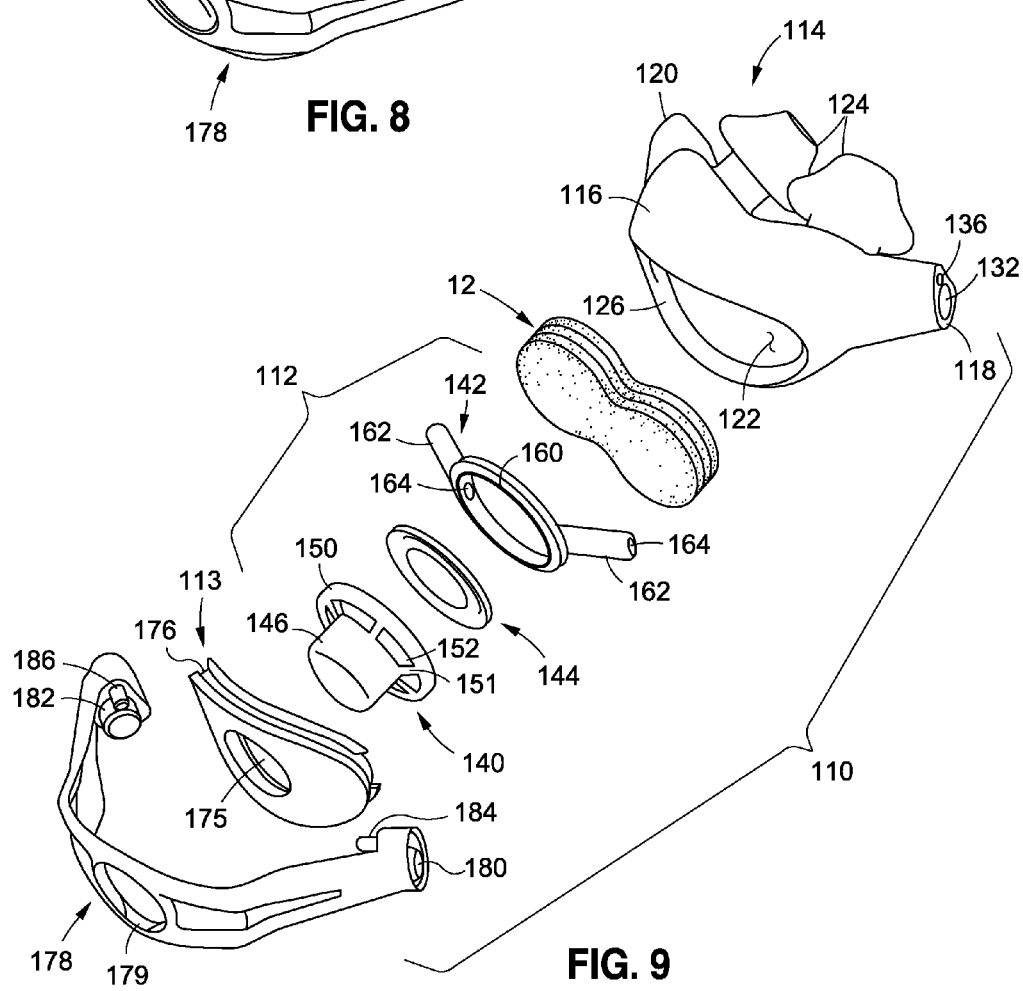
FIG. 9 is an exploded view of the nasal pillows mask shown in FIG. 8.
Figure 10:
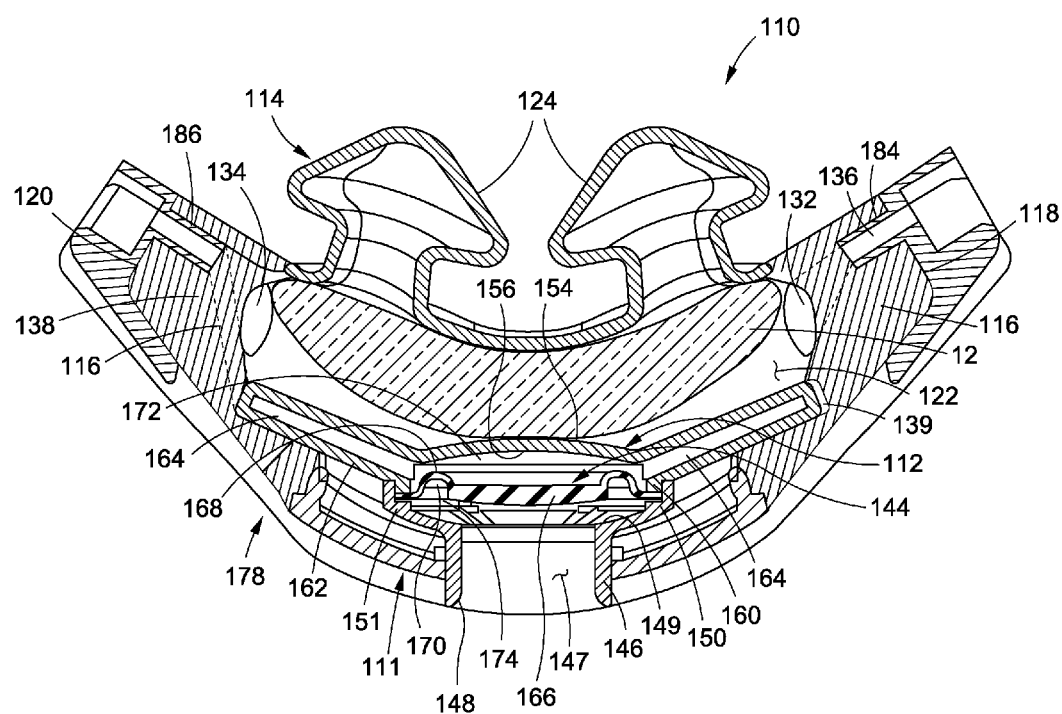
FIG. 10 is a partial cross-sectional view of the nasal pillows mask shown in FIG. 8, further depicting the flow pattern through the cushion of the mask and the heat and moisture exchange device disposed therein during an exhalation phase of a patient wearing the mask.

Referring now to FIGS. 8-10, there is shown a ventilation mask 110 (e.g., a nasal pillows mask) constructed in accordance with a third embodiment of the present invention. The mask 110 includes an integrated, diaphragm-implemented, piloted exhalation valve 112, the structural and functional attributes of which will be described in more detail below.

As shown in FIGS. 8-10, the mask 110 comprises a housing or cushion 114. The cushion 114, which is preferably fabricated from a silicone elastomer having a Shore A hardness in the range of from about 20 to 60 and preferably about 40, is formed as a single, unitary component, and is shown individually in FIG. 9. The cushion 114 includes a main body portion 116 which defines a first outer end surface 118 and an opposed second outer end surface 120. The main body portion 116 further defines an interior fluid chamber 122 which is of a prescribed volume. In addition to the main body portion 116, the cushion 114 includes an identically configured pair of hollow pillow portions 124 which protrude from the main body portion 116 in a common direction and in a prescribed spatial relationship relative to each other. More particularly, in the cushion 114, the spacing between the pillow portions 124 is selected to facilitate the general alignment thereof with the nostrils of an adult patient when the mask 110 is worn by such patient. Each of the pillow portions 124 fluidly communicates with the fluid chamber 122.

As shown in FIG. 9, the main body portion 116 of the cushion 114 includes an enlarged, circularly configured valve opening 126 which is in direct fluid communication with the fluid chamber 122. The valve opening 126 is positioned in generally opposed relation to the pillow portions 124 of the cushion 114. The valve opening 126 is adapted to accommodate an exhalation valve subassembly 111 of the mask 110 in a manner which will be described in more detail below.

The main body portion 116 of the cushion 114 further defines first and second gas delivery lumens 132, 134 which extend from respective ones of the first and second outer end surfaces 118, 120 into fluid communication with the fluid chamber 122. Additionally, a pressure sensing lumen 136 defined by the main body portion 116 extends from the first outer end surface 118 into fluid communication with the fluid chamber 122. The main body portion 116 further defines a valve pilot lumen 138 which extends from the second outer end surface 120 into fluid communication with the fluid chamber. Those of ordinary skill in the art will recognize that the gas delivery lumens 132, 134 may be substituted with a single gas delivery lumen and/or positioned within the cushion 114 in orientations other than those depicted in FIG. 10. For example, the gas delivery lumen(s) of the cushion 114 may be positioned frontally, pointing upwardly, pointing downwardly, etc. rather than extending laterally as shown in FIG. 10. The main body portion 116 of the cushion 114 further includes a mounting aperture 139 formed therein. As seen in FIG. 10, one end of the mounting aperture 139 communicates with the fluid chamber 122, with the opposite simply terminating blindly within the main body portion 116. The use of the first and second gas delivery lumens 132, 134, the pressure sensing lumen 136, the valve pilot lumen 138 and the mounting aperture 139 will be discussed in more detail below.

The exhalation valve subassembly 111 of the mask 110 comprises the aforementioned exhalation valve 112 in combination with a shield plate 113. The exhalation valve 112 of the mask 110 is itself made of three (3) parts or components, and more particularly a seat member 140, a cap member 142, and a diaphragm 144 which is operatively captured between the seat and cap members 140, 142. The seat and cap members 140, 142 are each preferably fabricated from a plastic material, with the diaphragm 144 preferably being fabricated from an elastomer having a Shore A hardness in the range of from about 20-40.

The seat member 140 includes a tubular, generally cylindrical wall portion 146 which defines a distal, annular outer rim 148 and an opposed annular inner seating surface 149. The wall portion further defines an outlet conduit 147 which extends between the outer rim 148 and seating surface 149. In addition to the wall portion 146, the seat member 140 includes an annular flange portion 150 which is integrally connected to the wall portion 146 by a series of spoke portions 151. The spoke portions 151 extend to locations on the wall portion 146 proximate the seating surface 149, with the flange portion 150 being positioned radially outward relative to the wall portion 146. In the seat member 140, the wall, flange and spoke portions 146, 150, 151 collectively define a plurality of exhaust vents 152 which are located about the periphery of the wall portion 146 in a prescribed arrangement and spacing relative to each other. The seat member 140 is formed such that each of the exhaust vents 152 normally fluidly communicates with the outlet conduit 147 defined by the wall portion 146.

The cap member 142 of the exhalation valve 112 comprises a circularly configured base portion 154 which defines an inner surface 156. In addition to the base portion 154, the cap member 142 includes an annular flange portion 160 which circumvents and protrudes generally perpendicularly relative to the inner surface 156 of the base portion 154. The cap member 142 further includes an identically configured pair of tube portions 162 which are integrally connected to the flange portion 160 in diametrically opposed relation to each other (i.e., approximately 180° apart). Each of the tube portions defines a lumen 164 extending therethrough and is used for reasons which will be discussed in more detail below. The seat and cap members 140, 142, when attached to each other in the fully assembled exhalation valve 112, collectively define an interior valve chamber of the exhalation valve 112, such valve chamber generally being located between the inner surface 156 defined by the base portion 154 of the cap member 142 and the seating surface 149 defined by the wall portion 146 of the seat member 140.

The diaphragm 144 of the exhalation valve 112, which resides within the valve chamber, has a circularly configured, central body portion 166, and a peripheral flange portion 168 which is integrally connected to and circumvents the body portion 166. The flange portion 168 includes an arcuately contoured primary region and a distal region which protrudes radially from the primary region. As such, the primary region of the flange portion 168 extends between the distal region thereof and the body portion 166, and defines a continuous, generally concave channel 170. The body portion 166 of the diaphragm 144 may optionally be perforated, i.e., be provided with an array of small apertures which extend therethrough.

In the exhalation valve 112, the flange portion 168 of the diaphragm 144 is operatively captured between complementary engagement surfaces defined by the flange portions 150, 160 of the seat and cap members 140, 142. More particularly, the annular distal region of the flange portion 168 is compressed (and thus captured) between an annular shoulder defined by the flange portion 160 of the cap member 142, and a complimentary annular shoulder which is defined by the flange portion 150 of the seat member 140 proximate the exhaust vents 152. The orientation of the diaphragm 144 within the valve chamber when captured between the seat and cap members 140, 142 is such that the channel 170 defined by the arcuately contoured primary region of the flange portion 168 is directed toward or faces the seating surface 149 defined by the wall portion 146 of the seat member 140.

The capture of the diaphragm 144 between the seat and cap members 140, 142 in the aforementioned manner results in the diaphragm 144 effectively segregating the valve chamber collectively defined by the seat and cap members 140, 142 into a pilot section 172 and an exhaust section 174. The pilot section 172 of the valve chamber is located between the diaphragm 144 and the inner surface 156 of the base portion 154 of the cap member 142. The exhaust section 174 of the valve chamber is located between the diaphragm 144 and both the exhaust vents 152 and the seating surface 149 of the wall portion 146 of the seat member 140. In this regard, the outlet conduit 147 defined by the wall portion 146 fluidly communicates with the exhaust section 174 of the valve chamber. In addition, the lumens 164 of the tube portions 162 of the cap member 142 each fluidly communicate with the pilot section 172 of the valve chamber.

The diaphragm 144 (and hence the exhalation valve 112) is selectively moveable between an open position and a closed position. When in its normal, open position, the diaphragm 144 is in a relaxed, unbiased state. Importantly, in either of its open or closed positions, the diaphragm 144 is not normally seated directly against the inner surface 156 defined by the base portion 154 of the cap member 142. Rather, a gap is normally maintained between the body portion 166 of the diaphragm 144 and the inner surface 156 of the base portion 154. The width of such gap when the diaphragm 144 is in its open position is generally equal to the fixed distance separating the inner surface 156 of the base portion 154 from the shoulder of the flange portion 160 which engages the distal region of the flange portion 168 of the diaphragm 144. Further, when the diaphragm 144 is in its open position, the body portion 166 is itself disposed in spaced relation to the seating surface 149 defined by the wall portion 146 of the seat member 140. As such, when the diaphragm 144 is in its open position, fluid is able to freely pass through the through the exhaust vents 152, between the seating surface 149 and diaphragm 144, and through the outlet conduit 147 defined by the wall portion 146 to ambient air.

In the exhalation valve 112, the diaphragm 144 is resiliently deformable from its open position (to which it may be normally biased) to its closed position. An important feature of the present invention is that the diaphragm 144 is normally biased to its open position which provides a failsafe to allow a patient to inhale ambient air through the exhalation valve 112 and exhale ambient air therethrough (via the exhaust vents 152) during any ventilator malfunction or when the mask 110 is worn without the therapy being delivered by the ventilator. When the diaphragm 144 is moved or actuated to its closed position, the periphery of the body portion 166 is firmly seated against the seating surface 149 defined by the wall portion 146 of the seat member 140. The seating of the body portion 166 of the diaphragm 144 against the seating surface 149 effectively blocks fluid communication between the outlet conduit 147 defined by the wall portion 146 and the exhaust section 174 of the valve chamber (and hence the exhaust vents 152 which fluidly communicate with the exhaust section 174).

In the mask 110, the cooperative engagement between the exhalation valve 112 and the cushion 114 is facilitated by the advancement of the cap member 142 into the valve opening 126 defined by the cushion 114. Subsequent to such advancement, one of the two tube portions 162 of the cap member 142 is partially advanced into and frictionally retained within the pilot lumen 138 of the cushion 114 in the manner shown in FIG. 10. The advancement of one tube portion 162 of the cap member 142 into the pilot lumen 138 facilitates the placement of the pilot lumen 138 into fluid communication with the pilot section 172 of the valve chamber via the lumen 164 of the corresponding tube portion 162. The remaining tube portion 162 of the cap member 142 (i.e., that tube portion 162 not advanced into the pilot lumen 138) is advanced into and frictionally retained within the above-described mounting aperture 139 in the manner shown in FIG. 10. Importantly, the resilient construction of the cushion 114, and in particular the main body portion 116 thereof, allows for the cushion 114 to be bent, twisted or otherwise manipulated as is needed to facilitate the advancement of the tube portions 162 of the cap member 142 into respective ones of the pilot lumen 138 and mounting aperture 139 in the aforementioned manner. The advancement of the tube portions 162 into respective ones of the pilot lumen 138 and mounting aperture 139 causes the exhalation valve 112 to assume a position within the fluid chamber 122 of the cushion 114 as is best shown in FIG. 10. In this regard, the majority of the exhalation valve 112 resides within the fluid chamber 122, with the exception of a small distal section of the wall portion 146 of the seat member 140 which protrudes from the valve opening 126 of the cushion 114.

Due to the positioning of the majority of the exhalation valve 112 within the fluid chamber 122, the exhaust section 174 of the valve chamber is placed into direct fluid communication with the fluid chamber 122 via the exhaust vents 152. Thus, irrespective of whether the diaphragm 144 of the exhalation valve 112 is in its open or closed positions, the pilot lumen 138 of the cushion 114 is maintained in a constant state of fluid communication with the pilot section 172 of the valve chamber. Additionally, irrespective of whether the diaphragm 144 is in its open or closed positions, the fluid chamber 122 is maintained in a constant state of fluid communication with the exhaust section 174 of the valve chamber via the exhaust vents 152. When the diaphragm 144 is in its open position, the fluid chamber 122 is further placed into fluid communication with both the outlet conduit 147 (and hence ambient air) via the open flow path defined between the body portion 166 of the diaphragm 144 and the seating surface 149 of the wall portion 146 of the seat member 140. However, when the diaphragm 144 is moved to its closed position, the fluid communication between the fluid chamber 122 and outlet conduit 147 is effectively blocked by the sealed engagement of the body portion 166 of the diaphragm 144 against the seating surface 149 of the wall portion 146.

As indicated above, in addition to the exhalation valve 112, the exhalation valve subassembly 111 includes the shield plate 113. The shield plate 113 has a generally oval, slightly arcuate profile, and includes a circularly configured opening 175 within the approximate center thereof. Additionally, formed within the peripheral side surface of the shield plate 113 is an elongate groove or channel 176. In the mask 110, the shield plate 113 is adapted to be advanced into the valve opening 126 subsequent to the cooperative engagement of the exhalation valve 112 to the cushion 114 in the aforementioned manner. More particularly, the advancement of the shield plate 113 into the valve opening 126 is facilitated in a manner wherein the wall portion 146 of the seat member 140 is advanced into and through the opening 175 of the shield plate 113. In this regard, the wall portion 146 and the opening 175 have complimentary configurations, with the diameter of the opening 175 only slightly exceeding that of the outer diameter of the wall portion 146.

Subsequent to the advancement of the wall portion 146 into the opening 175, that peripheral edge or lip of the main body portion 116 of the cushion 114 defining the valve opening 126 is advanced into and firmly seated within the complimentary channel 176 formed in the peripheral side surface of the shield plate 113. The receipt of such edge or lip of the cushion 114 into the channel 176 maintains the shield plate 113 in firm, frictional engagement to the cushion 114. The spatial relationship between the exhalation valve 112 and shield plate 113 when each is cooperatively engaged to the cushion 114 in the aforementioned manner is such that the distal section of the wall portion 146 which defines the outer rim 148 thereof protrudes slightly from the exterior surface of the shield plate 113.

As will be recognized, the shield plate 113, when cooperatively engaged to the cushion 114, effectively encloses that portion of the fluid chamber 122 which would otherwise be directly accessible via the valve opening 126. Importantly, by virtue of the attachment of the shield plate 113 to the main body portion 116 of the cushion 114, virtually the entirety of the exhalation valve 112 is completely enclosed or contained within the fluid chamber 122 of the cushion 114. As indicated above, only a small distal section of the wall portion 146 of the seat member 140 protrudes from the shield plate 113, and in particular the opening 175 defined thereby. As a result, the exhaust vents 152 which facilitate the fluid communication between the fluid chamber 122 and the exhaust section 174 of the valve chamber, and between the fluid chamber 122 and the outlet conduit 147 (and hence ambient air) when the diaphragm 144 is in the open position, are effectively enclosed within the fluid chamber 122 as provides noise attenuation advantages which will be discussed in more detail below.

To assist in maintaining the cooperative engagement between the exhalation valve subassembly 111 and the cushion 114, the mask 110 is further preferably provided with an elongate reinforcement frame member 178 which is attached to the cushion 114. The frame member 178 has a generally U-shaped configuration, with a central portion thereof including a circularly configured opening 179 formed therein which is adapted to accommodate that aforementioned distal section of the wall portion 146 of the seat member 140 which protrudes from the shield plate 113. In this regard, the diameter of the opening 179 is sized so as to only slightly exceed the outer diameter of the wall portion 146. The thickness of the central portion of the frame member 178 is such that when attached to cushion 114 subsequent to the advancement of the wall portion 146 into the complementary opening 179, the outer rim 148 defined by the wall portion 146 is substantially flush or continuous with the exterior surface of the frame member 178.

As shown in FIG. 10, the opposed end portions of the frame member 178 are cooperatively engaged to respective ones of the first and second outer end surfaces 118, 120 of the cushion 114. More particularly, the frame member 178 includes an identically configured pair of first and second connectors 180, 182 which are formed on respective ones of the opposed end portions thereof. An inner portion of the first connector 180 is advanced into and frictionally retained within the first gas delivery lumen 132 of the cushion 114. Similarly, an inner portion of the second connector 182 is advanced into and frictionally retained within the second gas delivery lumen 134 of the cushion 114. In addition to the inner portions advanced into respective ones of the first and second gas delivery lumens 132, 134, the first and second connectors 180, 182 of the frame member 178 each further include an outer portion which is adapted to be advanced into and frictionally retained within a corresponding lumen of a respective one of a pair of bi-lumen tubes fluidly coupled to the mask 110, in the same manner as described in detail above in relation to the mask 10.

The frame member 178 further includes a tubular, cylindrically configured pressure port 184 which is disposed adjacent the first connector 180. The pressure port 184 is aligned and fluidly communicates with the pressure sensing lumen 136 of the cushion 114. Similarly, the frame member 178 is also provided with a tubular, cylindrically configured pilot port 186 which is disposed adjacent the second connector 182. The pilot port 186 is aligned and fluidly communicates with the valve pilot lumen 138 of the cushion 114. The pressure and pilot ports 184, 186 of the frame member 78 are adapted to be placed into fluid communication with corresponding lumens of respective ones of the aforementioned pair of bi-lumen tubes which are fluidly connected to the mask 110 within a ventilation system incorporating the same, also in the same manner as described in detail above in relation to the mask 10. The receipt of the wall portion 146 of the seat member 140 into the opening 179 of the frame member 178 ensures that the cushion 114, the exhalation valve subassembly 111 and the frame member 178 are properly aligned, and prevents relative movement therebetween.

In the mask 110, the exhalation valve 112 is piloted, with the movement of the diaphragm 144 to the closed position described above being facilitated by the introduction of positive fluid pressure into the pilot section 172 of the valve chamber. More particularly, it is contemplated that during the inspiratory phase of the breathing cycle of a patient wearing the mask 110, the valve pilot lumen 138 will be pressurized by a pilot line fluidly coupled to the pilot port 186, with pilot pressure being introduced into that portion of the pilot section 172 of the valve chamber via the pilot lumen 138 and the lumen 164 of that tube portion 162 of the cap member 142 advanced into the pilot lumen 138. The fluid pressure level introduced into the pilot section 172 of the valve chamber will be sufficient to facilitate the movement of the diaphragm 144 to its closed position described above. When the diaphragm 144 is in its closed position, fluid pressure introduced into the fluid chamber 122 via the gas delivery lumens 132, 134 is prevented from being exhausted to ambient air. In this regard, though such fluid may flow from the fluid chamber 122 into the exhaust section 174 of the valve chamber via the exhaust vents 152, the engagement of the diaphragm 144 to the seating surface 149 defined by the wall portion 146 of the seat member 140 effectively blocks the flow of such fluid into the outlet conduit 147 defined by the wall portion 146 and hence to ambient air.

Conversely, during the expiratory phase of the breathing cycle of the patient wearing the mask 110, it is contemplated that the discontinuation or modulation of the fluid pressure through the valve pilot lumen 138 and hence into the pilot section 172 of the valve chamber, coupled with the resiliency of the diaphragm 144 and/or positive pressure applied to the body portion 166 thereof, will facilitate the movement of the diaphragm 144 back to the open position or to a partially open position. In this regard, positive pressure as may be used to facilitate the movement of the diaphragm 144 to its open position may be provided by air which is exhaled from the patient during the expiratory phase of the breathing circuit and is applied to the body portion 166 of the diaphragm 144 via the pillows portions 124 of the cushion 114, the fluid chamber 122, the exhaust vents 152, and the exhaust section 174 of the valve chamber. As will be recognized, the movement of the diaphragm 144 to the open position allows the air exhaled from the patient into the fluid chamber 122 via the pillow portions 124 to be vented to ambient air after flowing from the fluid chamber 122 into the exhaust section 174 of the valve chamber via the exhaust vents 152, and thereafter flowing from the exhaust section 174 between the diaphragm 144 and seating surface 149 of the wall portion 146 into the outlet conduit 147 also defined by the wall portion 146.

As will be recognized, based on the application of pilot pressure thereto, the diaphragm 144 travels from a fully open position through a partially open position to a fully closed position. In this regard, the diaphragm 144 will be partially open or partially closed during exhalation to maintain desired ventilation therapy. Further, when pilot pressure is discontinued to the diaphragm 144, it moves to an open position wherein the patient can inhale and exhale through the mask 110 with minimal restriction and with minimal carbon dioxide retention therein. This is an important feature of the present invention which allows a patient to wear the mask 110 without ventilation therapy being applied to the mask 110, the aforementioned structural and functional features of the mask 110 making it more comfortable to wear, and further allowing it to be worn without carbon dioxide buildup. This feature is highly advantageous for the treatment of obstructive sleep apnea wherein patients complain of discomfort with ventilation therapy due to mask and pressure discomfort. When it is detected that a patient requires sleep apnea therapy, the ventilation therapy can be started (i.e., in an obstructive sleep apnea situation).

To succinctly summarize the foregoing description of the structural and functional features of the mask 110, during patient inhalation, the valve pilot lumen 138 is pressurized, which causes the diaphragm 144 to close against the seating surface 149, thus effectively isolating the fluid chamber 122 of the mask 110 from the outside ambient air. The entire flow delivered from a flow generator fluidly coupled to the mask 110 is inhaled by the patient, assuming that unintentional leaks at the interface between the cushion 114 and the patient are discarded. This functionality differs from what typically occurs in a conventional CPAP mask, where venting to ambient air is constantly open, and an intentional leak flow is continuously expelled to ambient air. During patient exhalation, the pilot pressure introduced into the valve pilot lumen 138 is controlled so that the exhaled flow from the patient can be exhausted to ambient air through the exhalation valve 112 in the aforementioned manner. In this regard, the pilot pressure is "servoed" so that the position of the diaphragm 144 relative to the seating surface 149 is modulated, hence modulating the resistance of the exhalation valve 112 to the exhaled flow and effectively ensuring that the pressure in the fluid chamber 122 of the mask 110 is maintained at a prescribed therapeutic level throughout the entire length of the exhalation phase. When the valve pilot lumen 138 is not pressurized, the exhalation valve 112 is in a normally open state, with the diaphragm 144 being spaced from the seating surface 149 in the aforementioned manner, thus allowing the patient to spontaneously breathe in and out with minimal pressure drop (also referred to as back-pressure) in the order of less than about 2 cm $H_2O$ at 60 l/min. As a result, the patient can comfortably breathe while wearing the mask 110 and while therapy is not being administered to the patient. Importantly, the effective containment of the exhaust vents 152 within the fluid chamber 122 substantially mitigates or suppresses the noise generated by the mask 110 attributable to the flow of fluid into the exhaust section 174 of the valve chamber via the exhaust vents 152.

In the mask 110, it is contemplated that exhalation valve subassembly 111, and in particular the exhalation valve 112, may be detached from the cushion 114 and removed from within the fluid chamber 122 as needed for periodic cleaning or replacement thereof. As will be recognized, such removal is facilitated by first detaching the shield plate 113 from the cushion 114 by removing the lip of the cushion 114 defining the valve opening 126 from within the channel 176 of the shield plate 113. Thereafter, the exhalation valve 112 is simply grasped and pulled from within the fluid chamber 122, the flexibility/resiliency of the cushion 114 allowing for the easy removal of the tube portions 162 of the cap member 142 from within respective ones of the pilot lumen 138 and mounting aperture 139. The re-attachment of the exhalation valve subassembly 111 to the cushion 114 occurs in the reverse sequence, the exhalation valve 112 being advanced into the fluid chamber 122 and attached to the cushion 114 in the aforementioned manner prior to the attachment of the shield plate 113 to the cushion 114 in the aforementioned manner.

As further shown in FIGS. 9 and 10, the mask 110 also includes the above-described HME device 12 integrated therein. More particularly, the HME device 12 is positioned within the fluid chamber 122 of the cushion 114, and has both the shape and layered construction described with particularly above in relation to the mask 10. Prior to its advancement into the fluid chamber 122 of the cushion 114, the HME device 12 has the generally flat or planar profile shown in FIG. 9. The HME device 12 is operative to partially or completely replace a humidifier (cold or heated pass-over; active or passive) which would otherwise be fluidly coupled to the mask 110. This is possible because the average flow through the system envisioned to be used in conjunction with the mask 110 is about half of a prior art CPAP mask, due to the absence of any intentional leak in such system.

The size and shape of the HME device 12 relative to the shape and internal volume of the fluid chamber 122 is selected such that the HME device 12 assumes a prescribed contour or profile when operatively positioned within the fluid chamber 122. In the mask 110, the advancement of the HME device 12 into the fluid chamber 122 occurs prior to the operative engagement of the exhalation valve subassembly 111 to the cushion 114 in the above-described manner. In this regard, prior to the cooperative engagement of the exhalation valve subassembly 111 to the cushion 114, the HME device 12 is advanced into the fluid chamber 122 via the valve opening 126 defined by the cushion 114. Though, as is apparent from FIG. 9, the size of the HME device 12 exceeds that of the valve opening 126, the pliable nature of the material(s) preferably used for the layers 92, 94, 96 of the HME device 12 allows the same to be compressed and/or folded in a manner which facilitates the advancement through the valve opening 126 and into the fluid chamber 122.

When the HME device 12 is operatively positioned within the fluid chamber 122, at least portions of the continuous peripheral side surface of the HME device 12 are abutted against corresponding regions of the interior surface of the main body portion 116 of the cushion 114 which defines the fluid chamber 122. For instance, as seen in FIG. 10, portions of the peripheral side surface of the HME device 12 defined by each of the opposed end portions 88 thereof are abutted against corresponding interior surface regions of the main body portion 116 which are located between the inlet ends of respective ones of the first and second gas delivery lumens 132, 134, and corresponding ones of the pillow portions 124. In this regard, the size and shape of the HME device 12 is preferably such that when fully deployed within the fluid chamber 122, the HME device 12 will form a complete or substantially complete barrier between the open interiors of the pillow portions 124 and the fluid chamber 122, yet will not obstruct the inlet ends of either of the first and second gas delivery lumens 132, 134.

In addition to at least portions of the peripheral side surface of the HME device 12 being abutted against corresponding regions of that interior surface of the main body portion 116 defining the fluid chamber 122, it is also contemplated that a portion of the bottom surface of the HME device 12 (as viewed from the perspective shown in FIG. 10) as defined by the low density layer 92 thereof will be abutted against the base portion 154 of the cap member 142 of the exhalation valve 112 upon the cooperative engagement of the exhalation valve subassembly 111 to the cushion 114. Further, as also viewed from the perspective shown in FIG. 10, a portion of the top surface of the HME device 12 as defined by the high density layer 96 thereof is abutted against a portion of the interior surface of the main body portion 116 which is defined by that segment thereof extending between the pillow portions 124. The abutment of the opposed top and bottom surfaces of the HME device 12 against the main body portion 116 of the cushion 114 and cap member 142 of the exhalation valve 112 in the aforementioned manner, coupled with the abutment of the peripheral side surface of the HME device 12 against the main body portion 116, results in the HME device 12 assuming and being maintained in the arcuately shaped profile shown in FIG. 10. As indicated above, when it assumes the position shown in FIG. 10, the HME device 12 effectively segregates or separates the open interiors of the pillow portions 124 of the cushion 114 from the fluid chamber 122.

During an inhalation phase of a patient using the mask 110, air enters the fluid chamber 122 via the first and second gas delivery lumens 132, 134 which, as indicated above, are preferably unobstructed by the HME device 12. Due to the permeability of the HME device 12, the air is able to pass through the HME device 12 and into the nostrils of the patient via the pillow portions 124 of the cushion 114 similar to the flow path identified by the arrows shown in FIG. 3. Moisture and heat retained by the HME device 12 is transferred into the air passing there through prior to the air reaching the nostrils of the patient. Though air delivered into the fluid chamber 122 via the first and second gas delivery lumens 132, 134 is also capable of flowing into the exhalation valve 112, during the inhalation phase of the patient, the exhalation valve 112 is normally maintained in its closed position as described above. As a result, any gas entering the exhalation valve 112 during the inhalation phase is prevented from being vented via the exhaust vents 152 as a result of the diaphragm 144 being sealed against the seat member 140 in the aforementioned manner.

In the mask 110 having the HME device 12 positioned in the cushion 114 in the aforementioned manner, the size and shape of the HME device 12 relative to the shape and internal volume of the fluid chamber 122 is also selected such that the resultant shape of that portion of the fluid chamber 122 which is separated from the pillow portions 124 by the HME device 12 is operative to maximize flow over the exposed portions of the bottom surface of the HME device 12 defined by the low density layer 92 thereof. Such shape is also selected to impart a prescribed measure of turbulence to the air flowing into the fluid chamber 122 via the inlet ends of the first and second gas delivery lumens 132, 134. This turbulence, and the vortices resulting therefrom, assists in maximizing flow over the exposed portions of the bottom surface of the HME device 12. This in turn optimizes the level of moisture and heat transferred into the air passing through the HME device 12 and to the patient via the pillows portions 124 during the inhalation phase of the patient. An exemplary airflow pattern during the inhalation phase of the patient is also similar to that shown by the arrows included in FIG. 3.

During the exhalation phase of the patient wearing the mask 110, exhaled air travels through the open interiors of the pillow portions 124 and into the exhalation valve 112 through the HME device 12. Along these lines, the material(s) preferably used to facilitate the fabrication of the HME device 12 provide for the easy passage of exhaled air through the HME device 12 and into the exhalation valve 112 without causing the patient to exert any greater exhalation force, i.e., the patient does not sense that there is an obstruction within the mask 110 during the exhalation phase. As explained above, during the exhalation phase, the diaphragm 144 of the exhalation valve 112 is actuated to its open position, thus allowing air passing through the HME device 12 to be vented to ambient via the vent ports 152, the exhaust section 174, and the outlet conduit 147 of the exhalation valve 112. As will be recognized, the HME device 12 is operative to retain moisture and heat from the air exhaled by the patient and passing therethrough during the exhalation phase, and to transfer such moisture and heat to the patient in the aforementioned manner during the inhalation phase.

It is contemplated that the HME device 12 can be permanently assembled to the cushion 114, or may alternatively be removable therefrom and thus washable and/or disposable. In this regard, the HME device 12, if removable from within the cushion 114, could be replaced on a prescribed replacement cycle. Along these lines, it is further contemplated that the HME device 12 may be impregnated with a chemical agent which facilitates a color change therein when certain conditions are satisfied indicative of a need for the replacement thereof. Additionally, it is contemplated that the HME device 12 can be used as an elastic member that adds elasticity to the cushion 114. In this regard, part of the elasticity of the cushion 114 may be attributable to its silicone construction, and further be partly attributable to the compression and deflection of the HME device 12 inside the cushion 114. Still further, it is contemplated that the HME device 12 may be infused with any one of a number of different scents which may be chosen by the patient according to preference.

Figure 11:
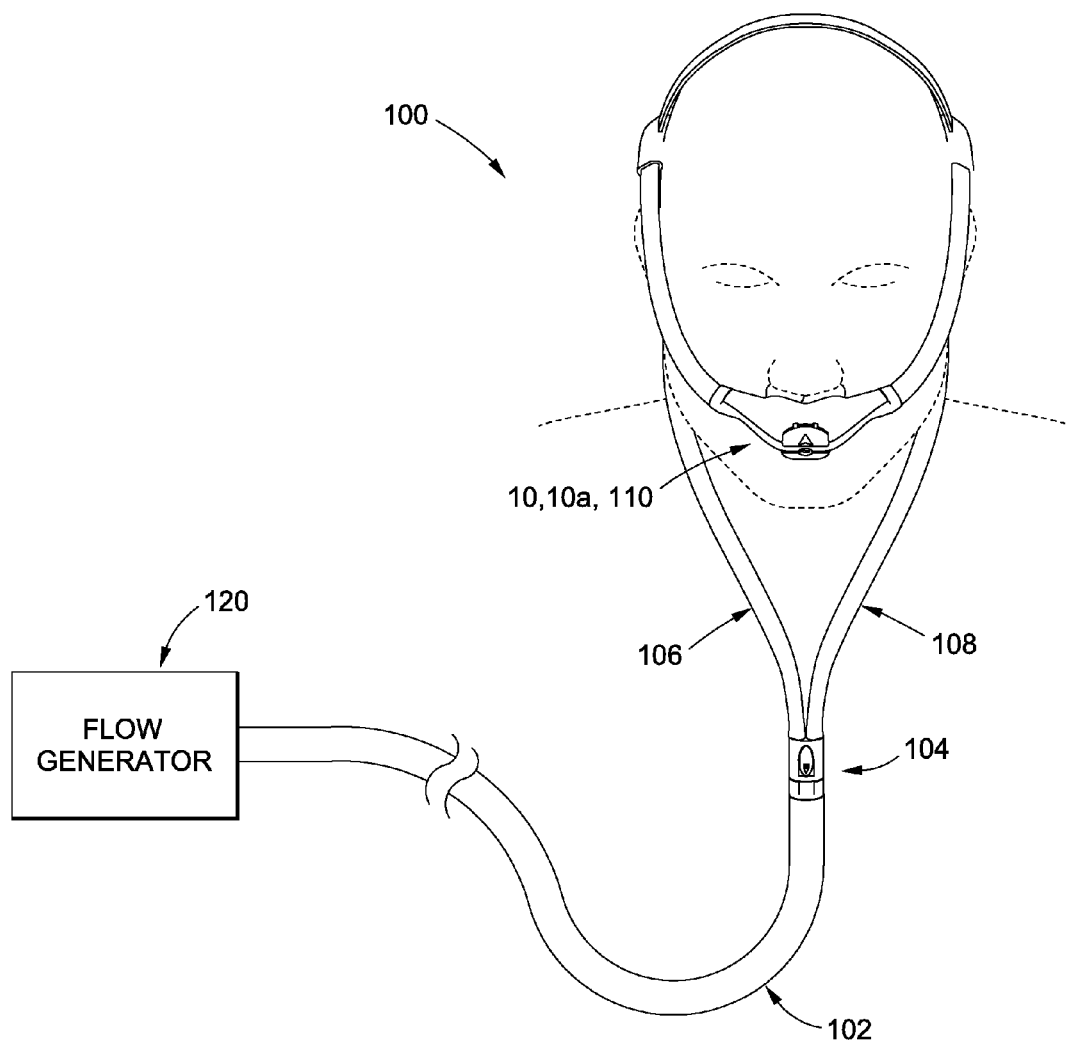
FIG. 11 is a front-elevational view of the nasal pillows mask constructed in accordance with either the first, second or third embodiments of the present invention, and further depicting an exemplary tri-lumen tube, Y-connector, and pair of bi-lumen tubes which are used to collectively facilitate the operative interface between the nasal pillows mask and a flow generating device.

Referring now to FIG. 11, there is shown a front-elevational view of the nasal pillows mask 10, 10a, 110 of the present invention as integrated into an exemplary ventilation system 100 wherein a tri-lumen tube 102, Y-connector 104, and pair of bi-lumen tubes 106, 108 are used to collectively facilitate the operative interface between the nasal pillows mask 10, 10a, 110 and a flow generating device or flow generator 120. In the ventilation system 100, the tri-lumen tube 102 is used to facilitate the fluid communication between the Y-connector 104 and the flow generator 120, with one end of the tri-lumen tube 102 being fluidly connected to the flow generator 120, and the opposite end thereof being fluidly connected to the Y-connector 104. The bi-lumen tubes 106, 108 are used to facilitate the fluid communication between the Y-connector 104 and the mask 10, 10a, 110 with one end of each of the bi-lumen tubes 106, 108 being fluidly connected to the Y-connector 104, and the opposite end thereof being fluidly connected to the mask 10, 10a, 110. A detailed description of the structural and functional attributes of the tri-lumen tube 102, Y-connector 104 and bi-lumen tubes 106, 108, as well as the manner in which the bi-lumen tubes 106, 108 are operatively connected to the mask 10, 10a, is described with particularity in Applicant's co-pending U.S. patent application Ser. No. 13/572,368 entitled VENTILATION MASK WITH INTEGRATED PILOTED EXHALATION VALVE filed Aug. 10, 2012, the disclosure of which is also incorporated herein by reference.

In each of the masks 10, 10a, 100 the integration of the exhalation valve 14, 112 into the cushion 16, 114 allows lower average flow compared to prior art CPAP masks. In this regard, the structural/functional features of the exhalation valve 14, 112 ensure that all the exhaled gas of the patient goes to ambient. As a result, a vent flow is not needed for flushing any trapped carbon dioxide out of the system. Further, during inspiration the exhalation valve 14, 112 can close, and the flow generator 120 of the system needs to deliver only the patient flow, without the additional overhead of the intentional leak flow. In turn, the need for lower flow rates allows for the use of smaller tubes that have higher pneumatic resistance, without the need for the use of extremely powerful flow generators. The pneumatic power through the system 100 can be kept comparable to those of traditional CPAP machines, though the pressure delivered by the flow generator 120 will be higher and the flow lower.

In addition, the reduced average flow through the system 100 in which the mask 10, 10a, 110 is used means that less humidity will be removed from the system 100, as well as the patient. Conventional CPAP systems have to reintegrate the humidity vented by the intentional leak using a humidifier, with heated humidifiers being the industry standard. Active humidification introduces additional problems such as rain-out in the system tubing, which in turn requires heated tubes, and thus introducing more complexity and cost into the system. The system 100 of the present invention, as not having any intentional leak flow, does not need to introduce additional humidity into the system. As indicated above, the HME device 12, 12a can be introduced directly into the cushion 16, 114 of the mask 10, 10a, 110 so that exhaled humidity can be trapped and used to humidify the air for the following breath. Because of its integration directly into the cushion 16, 114 of the mask 10, 10a, 110 in extremely close proximity to the patient's nostrils, the HME device 12, 12a optimizes the desired heat and moisture exchange operation with air inhaled and exhaled by a patient wearing the mask 10, 10a, 110.

This disclosure provides exemplary embodiments of the present invention. The scope of the present invention is not limited by these exemplary embodiments. Numerous variations, whether explicitly provided for by the specification or implied by the specification, such as variations in structure, dimension, type of material and manufacturing process may be implemented by one of skill in the art in view of this disclosure.

What is claimed is:

1. A nasal pillows mask, comprising:
   a cushion defining an internal fluid chamber, a pair of pillow portions defining open interiors therein which each fluidly communicate with the fluid chamber, and at least one gas delivery lumen which fluidly communicates with the fluid chamber, the at least one gas delivery lumen having a fluid inlet end proximate the fluid chamber; and
   a heat and moisture exchange device disposed within the fluid chamber of the cushion proximate the open interiors of the pillow portions thereof, wherein the heat and moisture exchange device is configured to at least partially segregate the open interiors of the pillow portions from the fluid chamber and further configured so as not to cover the fluid inlet end of the at least one gas delivery lumen and to extend at least partially between the at least one gas delivery lumen and the open interiors of the pillow portions.

2. The nasal pillows mask of claim 1 further comprising:
   a valve pilot lumen defined by the cushion; and
   an exhalation valve cooperatively engaged to the cushion in a manner wherein the valve pilot lumen is fluidly coupled thereto, the exhalation valve being fluidly coupled to the fluid chamber;
   the exhalation valve being piloted, and selectively movable between a closed position wherein fluid flow between the fluid chamber and ambient air is at least partially obstructed thereby, and an open position wherein at least a portion of the fluid chamber is vented to ambient air.

3. The nasal pillows mask of claim 2 wherein the heat and moisture exchange device is permanently attached to the exhalation valve.

4. The nasal pillows mask of claim 3 wherein the heat and moisture exchange device has a generally frusto-conical configuration.

5. The nasal pillows mask of claim 1 wherein the heat and moisture exchange device is further configured to fully segregate the pillow portions from the fluid chamber.

6. The nasal pillows mask of claim 1 wherein:
   the cushion defines first and second gas delivery lumens which each fluidly communicate with the fluid chamber, the first and second gas delivery lumens each having a fluid inlet end proximate the fluid chamber; and
   the heat and moisture exchange device is further configured so as not to cover the fluid inlet end of either of the first and second gas delivery lumens.

7. The nasal pillows mask of claim 1 wherein:
   the cushion further defines a pressure sensing lumen which fluidly communicates with the fluid chamber; and
   the heat and moisture exchange device is further configured so as not to cover the pressure sensing lumen.

8. The nasal pillows mask of claim 1 wherein:
   the fluid chamber is formed to be of a prescribed shape and internal volume; and
   the heat and moisture exchange device is configured relative to the shape and internal volume of the fluid chamber such that fluid flowing into the fluid chamber from the gas delivery lumen has a prescribed pattern of turbulence imparted thereto.

9. The nasal pillows mask of claim 1 wherein the heat and moisture exchange device has a multi-layer construction.

10. The nasal pillows mask of claim 9 wherein the heat and moisture exchange device comprises:
    a high density layer;
    a low density layer; and
    a medium density layer captured between the high and low density layers;
    the heat and moisture exchange device being oriented within the fluid chamber such that the high density layer is disposed closest to the pillow portions of the cushion.

11. A nasal pillows mask, comprising:
    a cushion defining at least one flow passage, wherein the cushion defines first and second gas delivery lumens which each fluidly communicate with the flow passage, the first and second gas delivery lumens each having a fluid inlet end proximate the flow passage, wherein the cushion further defines at least one delivery section that channels fluid flowing into the flow passage from the first and second gas delivery lumens into a nose of a patient; and a heat and moisture exchange device disposed within the flow passage;

wherein the heat and moisture exchange device is configured relative to the flow passage such that fluid flowing into the flow passage has a prescribed pattern of turbulence imparted thereto by the cushion and the heat and moisture exchange device and further configured so as not to cover the fluid inlet end of either of the first and second gas delivery lumens and to extend at least partially between the first and second gas delivery lumens and the at least one delivery section.

12. The nasal pillows mask of claim 11 further comprising:

an exhalation valve cooperatively engaged to the cushion and fluidly coupled to the flow passage;

the exhalation valve being selectively movable between a closed position wherein fluid flow between the flow passage and ambient air is at least partially obstructed thereby, and an open position wherein at least a portion of the flow passage is vented to ambient air.

13. The nasal pillows mask of claim 12 wherein the heat and moisture exchange device is permanently attached to the exhalation valve.

14. The nasal pillows mask of claim 11 wherein:

the cushion further defines a pressure sensing lumen which fluidly communicates with the flow passage; and the heat and moisture exchange device is further configured so as not to cover the pressure sensing lumen.

15. The nasal pillows mask of claim 11 wherein the heat and moisture exchange device has a multi-layer construction.

16. The nasal pillows mask of claim 15 wherein the heat and moisture exchange device comprises:

a high density layer;

a low density layer; and a medium density layer captured between the high and low density layers.

* * * * *